(12) United States Patent
Matsubara et al.

(10) Patent No.: US 6,495,701 B1
(45) Date of Patent: Dec. 17, 2002

(54) METHOD FOR MANUFACTURING TRICYCLIC AMINO ALCOHOL DERIVATIVES

(75) Inventors: Koki Matsubara, Miyazaki (JP); Hitoshi Kida, Miyazaki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/937,488

(22) PCT Filed: Mar. 21, 2000

(86) PCT No.: PCT/JP00/01696
§ 371 (c)(1),
(2), (4) Date: Sep. 26, 2001

(87) PCT Pub. No.: WO00/58287
PCT Pub. Date: Oct. 5, 2000

(30) Foreign Application Priority Data

Mar. 26, 1999 (JP) .......................................... 11-083197

(51) Int. Cl.$^7$ ............................................ C07D 209/82
(52) U.S. Cl. .......................... 548/439; 548/444; 549/48; 549/460
(58) Field of Search .................... 549/48, 460; 548/444, 548/439

(56) References Cited

U.S. PATENT DOCUMENTS

| | | | |
|---|---|---|---|
| 5,763,688 A | | 6/1998 | Ikariya et al. |
| 6,037,362 A | * | 3/2000 | Miyoshi et al. ............. 514/411 |
| 6,172,099 B1 | * | 1/2001 | Miyoshi et al. ............. 514/411 |
| 6,184,381 B1 | | 2/2001 | Ikariya et al. |

FOREIGN PATENT DOCUMENTS

| | | |
|---|---|---|
| EP | 0 882 707 A1 | 12/1998 |
| EP | 992707 | 12/1998 |
| EP | 997458 | 5/2000 |
| JP | A 4-187685 | 7/1992 |
| WO | 00/59885 | 10/2000 |

OTHER PUBLICATIONS

Kazushi Mashima et al., "Cationic BINAP–Ru (II) Halide Complexes: Highly Efficient Catalysts for Stereoselective Asymmetric Hydrogenation of α– and β–Functionalized Ketones," *J. Org. Chem.*, V. 59, 1994, pp. 3064–3076.

Shunji Sakuraba et al., "Efficient Asymmetric Hydrogenation of β– and γ–Amino Ketone Derivaties Leading to Practical Synthesis of Fluoxetine and Eprozinol," *Chem. Pharm. Bull.*, V. 43, No. 5, 1995, pp. 748–753.

* cited by examiner

*Primary Examiner*—Joseph K. McKane
*Assistant Examiner*—Kamal Saeed
(74) *Attorney, Agent, or Firm*—Young & Thompson

(57) ABSTRACT

The present invention is directed to processes for the preparation of a compound useful for treating diabetes, obesity, hyperlipidemia and the like, which compound is represented by the formula (1):

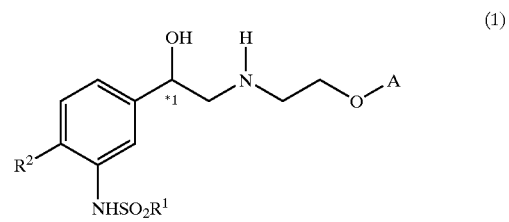

(1)

wherein $R^1$ represents a lower alkyl group or a benzyl group; *1 represents an asymmetric carbon atom; $R^2$ hydrogen atom, a halogen atom or a hydroxyl group; and A represents one of the following groups:

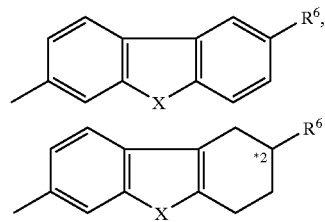

wherein X represents NH, O or S; $R^6$ represents a hydrogen atom, a hydroxyl group, an amino group or an acetylamino group; and *2 represents an asymmetric carbon atom when $R^6$ is not a hydrogen atom, and to intermediates useful for the said processes. The processes of the present invention are convenient, practical preparing processes with low cost which comprise a small number of steps with good industrial work efficiency.

13 Claims, No Drawings

METHOD FOR MANUFACTURING TRICYCLIC AMINO ALCOHOL DERIVATIVES

This is a 371 of International Application PCT/JP00/01696 filed Mar. 21, 2000.

FIELD OF THE INVENTION

The present invention relates to a novel process for the preparation of tricyclic amino-alcohol derivatives or salts thereof which are useful for treating and preventing diabetes, obesity, hyperlipidemia and the like and have the formula (1):

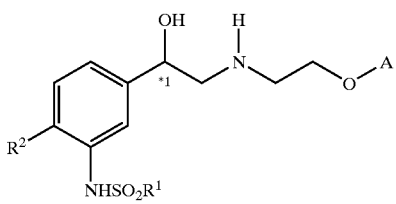

(1)

wherein
  R$^1$ represents a lower alkyl group or a benzyl group;
  *1 represents an asymmetric carbon atom;
  R$^2$ represents a hydrogen atom, a halogen atom or a hydroxyl group; and
  A represents one of the following groups:

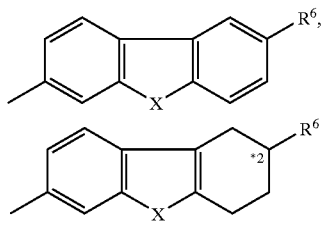

wherein X represents NH, O or S; R$^6$ represents a hydrogen atom, a hydroxyl group, an amino group or an acetylamino group; and *2 represents an asymmetric carbon atom when R$^6$ is not a hydrogen atom. This invention also relates to intermediates useful for the preparing process.

BACKGROUND OF THE INVENTION

JP-A-9-249623 (WO 97/25311) and WO 99/01431 describe in detail processes for the preparation of the compounds of the above-mentioned general formula (1) and also describe that these compounds are very useful for treating and preventing diabetes, obesity, hyperlipidemia and the like.

Problems to be Solved

However, the study of the above known processes carried out by the present inventors showed that the said processes were not necessarily a practical process. There has been a need for a convenient, practical preparing process with low cost which comprises a small number of steps with good industrial work efficiency.

Means to Solve the Problems

The study carried out by the present inventors showed some disadvantages involved in the conventional processes for preparing a compound of the formula (1) set forth above, wherein the disadvantages were that the processes required many reaction steps and several purifying works such as chromatography, and did not necessarily provide a good yield. In addition, if an optical isomer, such as R-form of a compound of the formula (1) is to be finally obtained according to the synthesizing route disclosed in the above patent publications, the carbonyl group is reduced with borane as a reducing agent in the presence of a chiral auxiliary agent represented by the following general formula (15):

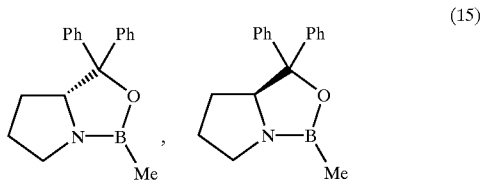

(15)

This chiral auxiliary agent is very expensive and the process for the preparation thereof is very complicated. Moreover, the chiral auxiliary agent is a hazardous combustible substance and an asymmetric reduction using the said chiral auxiliary agent requires strictly anhydrous conditions, strict temperature controls, complicated works and the like, which will become problematic when the chiral auxiliary agent is industrially used.

In order to solve the above problems, the present inventors examined a variety of synthesizing processes. As a result, the present inventors have established preferred synthesizing processes successfully and completed the present invention.

That is, the aspect of the first synthesizing route of the present invention is a process for the preparation of a compound of the formula (1):

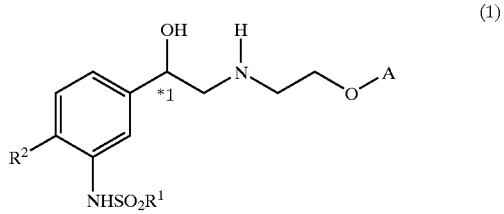

(1)

wherein R$^1$ represents a lower alkyl group or a benzyl group; R$^2$ represents a hydrogen atom, a halogen atom or a hydroxyl group; *1 represents an asymmetric carbon atom; and A represents one of the following groups:

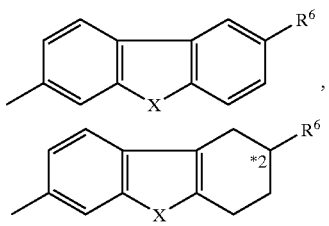

wherein X represents NH, O or S; R$^6$ represents a hydrogen atom, a hydroxyl group, an amino group or an acetylamino group; and *2 represents an asymmetric carbon atom when R$^6$ is not a hydrogen atom, which comprises the following steps (a) to (c):

(a)
i) reacting a compound of the formula (4):

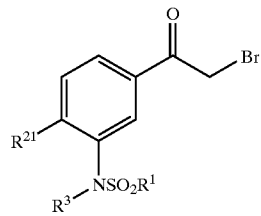
(4)

wherein $R^1$ is as defined above; $R^{21}$ represents a hydrogen atom, a halogen atom, a hydroxyl group or a protected hydroxyl group; $R^3$ represents an amino-protecting group or a hydrogen atom, with a compound of the formula (12):

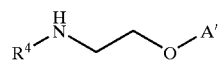
(12)

wherein $R^4$ represents an amino-protecting group or a hydrogen atom; and A' represents one of the following groups:

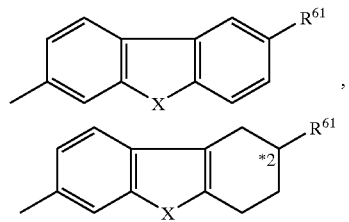

wherein X represents NH, O or S; $R^{61}$ represents a hydrogen atom, a protected hydroxyl group, a protected amino group or an acetylamino group; and *2 represents an asymmetric carbon atom when $R^{61}$ is not a hydrogen atom, to give a compound of the formula (3):

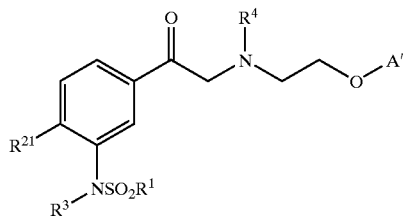
(3)

wherein $R^1$, $R^{21}$, $R^3$, $R^4$ and A' are as defined above; or
ii) coupling a compound of the formula (4) with a compound of the formula (14):

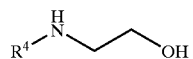
(14)

wherein $R^4$ is as defined above, to give a compound of the formula (6):

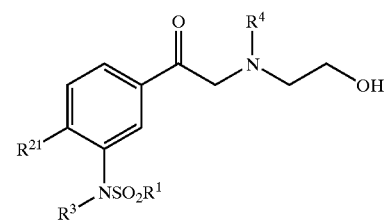
(6)

wherein $R^1$, $R^{21}$, $R^3$ and $R^4$ are as defined above; or
iii) further converting the primary hydroxyl group of the compound of the formula (6) into a leaving group $B^3$ to give a compound of the formula (5):

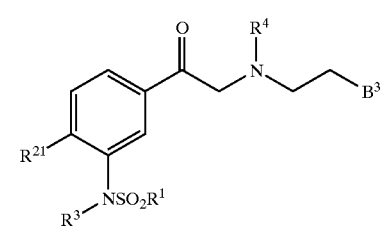
(5)

wherein $R^1$, $R^{21}$, $R^3$ and $R^4$ are as defined above, and $B^3$ represents a leaving group; or
iv) further reacting the resulting compound of the formula (5) with a compound represented by A'—OH wherein A' is as defined above to give a compound of the formula (3);
(b) then reducing the resulting compound of any one of the formulae (3), (5) and (6) to give a compound of the formula (2) as follows:
i) reducing the compound of the formula (3) to give an amino-alcohol of the formula (2):

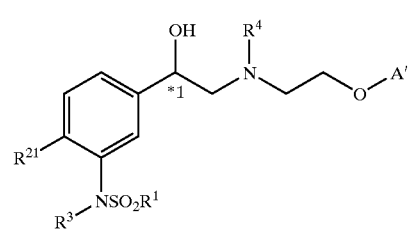
(2)

wherein $R^1$, $R^{21}$, $R^3$, $R^4$ and A' are as defined above, and *1 represents an asymmetric carbon atom; or
ii) reducing the compound of the formula (5) to give a compound of the formula (7):

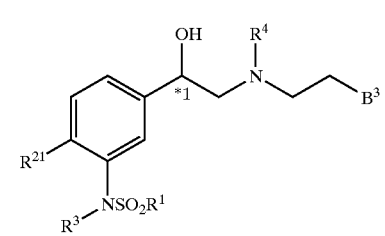
(7)

wherein $R^1$, $R^{21}$, $R^3$, $R^4$ and $B^3$ are as defined above, and *1 represents an asymmetric carbon atom, or
iii) reducing the compound of the formula (6) to give a compound of the formula (8):

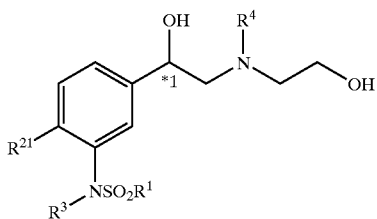

(8)

wherein $R^1$, $R^{21}$, $R^3$ and $R^4$ are as defined above, and *1 represents an asymmetric carbon atom, and converting the primary hydroxyl group of the resulting compound of the formula (8) into a leaving group $B^3$ to give a compound of the formula (7), then reacting the compound of the formula (7) obtained by either step as set forth above with a compound represented by A'—OH wherein A' is as defined above to give an amino-alcohol of the formula (2); and (c) simultaneously or sequentially removing the protecting groups of the compound of the formula (2) obtained by any one of processes as set forth above to give a compound of the formula (1).

The aspect of the first synthesizing route of the present invention is a process for the preparation of a compound of the above-mentioned general formula (1), which comprises the following steps (a) to (c):

(a) reacting a compound of the formula (4):

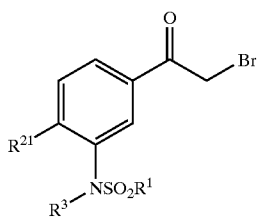

(4)

wherein $R^1$ is as defined above; $R^{21}$ represents a hydrogen atom, a halogen atom, a hydroxyl group or a protected hydroxyl group; $R^3$ represents an amino-protecting group or a hydrogen atom, with a compound of the formula (12):

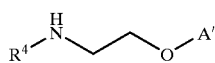

(12)

wherein $R^4$ represents an amino-protecting group or a hydrogen atom; and A' represents one of the following groups:

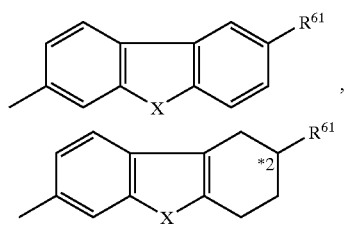

wherein X represents NH, O or S; R61 represents a hydrogen atom, a protected hydroxyl group, a protected amino group or an acetylamino group; and *2 represents an asymmetric carbon atom when $R^{61}$ is not a hydrogen atom, to give a compound of the formula (3):

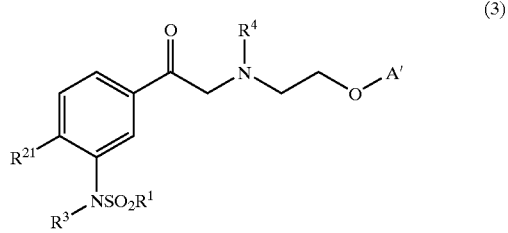

(3)

wherein $R^1$, $R^{21}$, $R^3$, $R^4$ and A' are as defined above;

(b) reducing the resulting compound of the formula (3) to give an amino-alcohol of the formula (2):

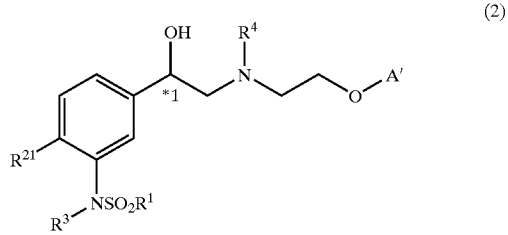

(2)

wherein $R^1$, $R^{21}$, $R^3$, $R^4$ and A' are as defined above, and *1 represents an asymmetric carbon atom; and (c) simultaneously or sequentially removing the protecting groups to give a compound of the formula (1).

In the aspect of the first synthesizing route set forth above, a compound represented by the formula (3) is the first preferred intermediate which is a novel compound and is relatively good in crystallinity. The said compound does not necessarily need a column chromatography purifying step and may be used in the following reaction step after being subjected to a recrystallizing treatment and the like.

Specific examples of a compound represented by the formula (3) include:

2-[N-benzyl-N-[2-(9H-carbazol-2-yloxy)]ethyl]amino-1-(3-methyl sulfonylamino)phenylethanone;
2-[N-benzyl-N-[2-(9H-carbazol-2-yloxy)]ethyl]amino-1-[3-(N-benzyl-N-methylsulfonylamino)]phenylethanone;
2-[N-benzyl-N-[2-(9H-carbazol-2-yloxy)]ethyl]amino-1-(4-benzyloxy-3-methylsulfonylamino)phenylethanone;
2-[N-benzyl-N-[2-(9H-carbazol-2-yloxy)]ethyl]amino-1-[4-benzyloxy-3-(N-benzyl-N-methylsulfonylamino)]phenylethanone;
2-[N-benzyl-N-[2-(9H-carbazol-2-yloxy)]ethyl]amino-1-(4-chloro-3-methylsulfonylamino)phenylethanone;
2-[N-benzyl-N-[2-(9H-carbazol-2-yloxy)]ethyl]amino-1-[4-chloro-3-(N-benzyl-N-methylsulfonylamino)]phenylethanone;
2-[N-benzyl-N-[2-(9H-carbazol-2-yloxy)]ethyl]amino-1-(4-bromo-3-methylsulfonylamino)phenylethanone;
2-[N-benzyl-N-[2-(9H-carbazol-2-yloxy)]ethyl]amino-1-[4-bromo-3-(N-benzyl-N-methylsulfonylamino)]phenylethanone;
2-[N-benzyl-N-[2-(6-benzyloxy-9H-carbazol-2-yloxy)]ethyl]amino-1-[3-(N-benzyl-N-methylsulfonylamino)]phenylethanone;
2-[N-benzyl-N-[2-(6-benzyloxy-9H-carbazol-2-yloxy)]ethyl]amino-1-[4-benzyloxy-3-(N-benzyl-N-methylsulfonylamino)]phenylethanone; and 2-[N-benzyl-N-[2-(6-benzyloxy-9H-carbazol-2-yloxy)]
ethyl]amino-1-(4-chloro-3-methylsulfonylamino)
phenylethanone.

The said examples also include:

2-[N-benzyl-N-[2-(dibenzothiophene-3-yloxy)]ethyl]
amino-1-(4-benzyloxy-3-methylsulfonylamino)
phenylethanone; and
2-[N-benzyl-N-[2-(dibenzothiophene-3-yloxy)]ethyl]
amino-1-[4-benzyloxy-3-(N-benzyl-N-
methylsulfonylamino)]phenylethanone.

In the steps set forth above, the step in which a compound of the formula (3) is reduced to give a compound of the formula (2) is a particularly characteristic of the present process.

In addition, when one of the optical isomers of a compound of the formula (1) is to be obtained in the steps set forth above, a compound of the formula (3) is preferably asymmetrically reduced. In this case, both of an amino-alcohol of the formula (2) and a compound of the formula (1) are obtained as one of their optical isomers, respectively. This is also characteristic of the present process.

Further, in the steps set forth above, the step in which a compound of the formula (4) is reacted with a compound of the formula (12) to give a compound of the formula (3) is also characteristic of the present process.

The aspect of the second synthesizing route of the present invention is a process for the preparation of a compound of the above-mentioned general formula (1), which comprises the following steps:

reacting a compound of the formula (4) with a compound of the formula (14):

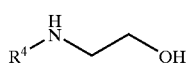
(14)

wherein $R^4$ is as defined above, to give a compound of the formula (6):

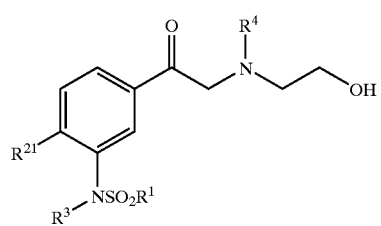
(6)

wherein $R^1$, $R^{21}$, $R^3$ and $R^4$ are as defined above; and
(i) converting the terminal hydroxyl group (the primary hydroxyl group) of the side-chain of the compound of the formula (6) into a leaving group $B^3$ to give a compound of the formula (5):

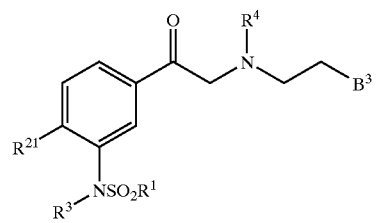
(5)

wherein $R^1$, $R^{21}$, $R^3$ and $R^4$ are as defined above, and $B^3$ represents a leaving group; and reacting the compound of the formula (5) with a compound represented by A'—OH wherein A' is as defined above to give a compound of the formula (3); or (ii) reacting the compound of the formula (6) with a compound represented by A'—OH according to Mitsunobu reaction to give a compound of the formula (3); and
then the compound of the formula (3), obtained by either step set forth above, is subjected to the sequential reaction steps as set forth above to give a compound of the formula (1) via a compound of the formula (2).

In the aspect of the second synthesizing route set forth above, a compound represented by the formula (18) including the formulae (6) and (5), is the second preferred intermediate which is a novel compound. The said compound does not necessarily need a column chromatography purifying step and may be used in the following reaction step after being subjected to a recrystallizing treatment and the like.

Specific examples of a compound represented by the formula (6) include:

2-[N-benzyl-N-(2-hydroxyethyl)]amino-1-[3-(N-benzyl-N-methylsulfonylamino)]phenylethanone;
2-[N-benzyl-N-(2-hydroxyethyl)]amino-1-[4-benzyloxy-3-(N-benzyl-N-methylsulfonylamino)]phenylethanone;
2-[N-benzyl-N-(2-hydroxyethyl)]amino-1-[4-chloro-3-(N-benzyl-N-methylsulfonylamino)]phenylethanone; and
2-[N-benzyl-N-(2-hydroxyethyl)]amino-1-[4-bromo-3-(N-benzyl-N-methylsulfonylamino)]phenylethanone.

Further, examples of a compound represented by the formula (5) include:

2-[N-benzyl-N-(2-bromoethyl)]amino-1-[3-(N-benzyl-N-methylsulfonylamino)]phenylethanone;
2-[N-benzyl-N-(2-bromoethyl)]amino-1-[4-benzyloxy-3-(N-benzyl-N-methylsulfonylamino)]phenylethanone;
2-[N-benzyl-N-(2-bromoethyl)]amino-1-[4-chloro-3-(N-benzyl-N-methylsulfonylamino)]phenylethanone; and
2-[N-benzyl-N-(2-bromoethyl)]amino-1-[4-bromo-3-(N-benzyl-N-methylsulfonylamino)]phenylethanone.

In the steps set forth above, the step in which a compound of the formula (4) is reacted with a compound of the formula (14) to give a compound of the formula (6) is also characteristic of the present process.

In the steps set forth above, the step in which a compound of the formula (6) is react with a compound represented by A'—OH according to Mitsunobu reaction to give a compound of the formula (3) is also characteristic of the present process.

The aspect of the third synthesizing route of the present invention is a process for the preparation of a compound of the above-mentioned general formula (1), which comprises the following steps:

reducing a compound of the formula (5) to give a compound of the formula (7):

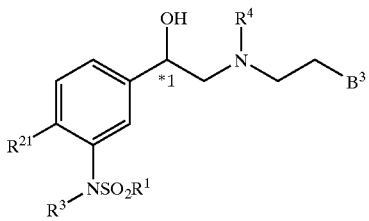

(7)

wherein $R^1$, $R^{21}$, $R^3$, $R^4$, $B^3$ and *1 are as defined above, which is then condensed with a compound represented by A'—OH to give an amino-alcohol of the formula (2). The amino-alcohol is subjected to the same reactions with those as set forth above to give a compound of the formula (1).

In this synthesizing route, the reduction of a compound of the formula (5) can be carried out by asymmetrically reducing method to give one of the optical isomers of a compound of the formula (7), which can be then subjected to the following steps to give one of the optical isomers of each compound of the formulae (2) and (1). These steps are characteristic of the present process.

In the aspect of the third synthesizing route set forth above, a compound of the formula (7), which is included within the formula (19), is novel and is the third preferred intermediate. The compound does not necessarily need a column chromatography purifying step and may be used in the following reaction step after being subjected to a recrystallizing treatment and the like.

Specific examples of a compound represented by the formula (7) include:

2-[N-benzyl-N-(2-bromoethyl)]amino-1-[3-(N-benzyl-N-methylsulfonylamino)]phenylethanol;
2-[N-benzyl-N-(2-bromoethyl)]amino-1-[4-chloro-3-(N-benzyl-N-methylsulfonylamino)]phenylethanol;
2-[N-benzyl-N-(2-bromoethyl)]amino-1-[4-bromo-3-(N-benzyl-N-methylsulfonylamino)]phenylethanol; and
2-[N-benzyl-N-(2-bromoethyl)]amino-1-[4-benzyloxy-3-(N-benzyl-N-methylsulfonylamino)]phenylethanol.

The aspect of the fourth synthesizing route of the present invention is a process for the preparation of a compound of the above-mentioned general formula (1), which comprises the following steps:

reducing a compound of the formula (6) to give a compound of the formula (8):

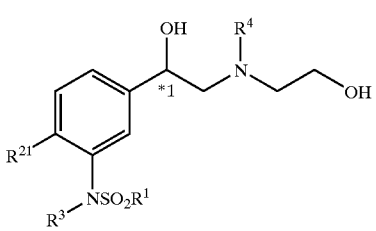

(8)

wherein $R^1$, $R^{21}$, $R^3$, $R^4$ and *1 are as defined above;
(i) converting the terminal hydroxyl group of the side-chain of the compound of the formula (8) into a leaving group $B^3$ to give a compound of the above-mentioned general formula (7), which was then condensed with a compound represented by A'—OH to give a compound of the formula (2); or (ii) reacting a compound of the formula (8) with a compound represented by A'—OH according to Mitsunobu reaction to give a compound of the formula (2); and subjecting the compound of the formula (2), obtained by either step, to deprotecting treatment as set forth above to give the compound of the formula (1).

In this synthesizing route, the reduction of a compound of the formula (6) can be carried out by asymmetrically reducing method to give one of the optical isomers of a compound of the formula (8), which can be then subjected to the following steps to give one of the optical isomers of each compound of the formulae (7), (2) and (1). These steps are characteristic of the present process.

In the aspect of the fourth synthesizing route set forth above, a compound of the formula (8), which is included within the formula (19), is novel and is the third preferred intermediate. The compound does not necessarily need a column chromatography purifying step and may be used in the following reaction step after being subjected to a recrystallizing treatment and the like.

Specific examples of a compound represented by the formula (8) include:

2-[N-benzyl-N-(2-hydroxyethyl)]amino-1-[3-(N-benzyl-N-methylsulfonylamino)]phenylethanol;
2-[N-benzyl-N-(2-hydroxyethyl)]amino-1-[4-benzyloxy-3-(N-benzyl-N-methylsulfonylamino)]phenylethanol;
2-[N-benzyl-N-(2-hydroxyethyl)]amino-1-[4-chloro-3-(N-benzyl-N-methylsulfonylamino)]phenylethanol; and
2-[N-benzyl-N-(2-hydroxyethyl)]amino-1-[4-bromo-3-(N-benzyl-N-methylsulfonylamino)]phenylethanol.

In the aspect of the fourth synthesizing route set forth above, the step in which a compound of the formula (8) is react with a compound represented by A'—OH according to Mitsunobu reaction to give a compound of the formula (2) is characteristic of the present process and is preferred.

Furthermore, the aspect of the fifth synthesizing route of the present invention is a process for the preparation of a compound of the above-mentioned general formula (1), which comprises the following steps:

condensing a compound of the formula (4) with a compound of the formula (13):

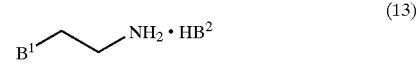

(13)

wherein $B^1$ and $B^2$ may be the same or different and represent a halogen atom, to give a compound of the formula (11):

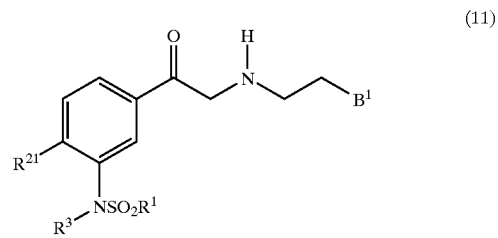

(11)

wherein $R^1$, $R^{21}$, $R^3$ and $B^1$ are as defined above;
reducing the compound of the formula (11) to give a compound of the formula (10):

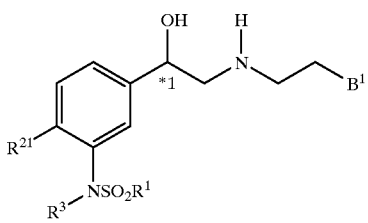

(10)

wherein $R^1$, $R^{21}$, $R^3$, $B^1$ and *1 are as defined above, and protecting the amino group of which is then protected with an amino-protecting group $R^5$, followed by condensing the compound with a compound represented by A'—OH to give a compound of the formula (9):

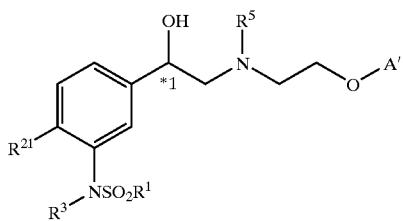

(9)

wherein $R^1$, $R^{21}$, $R^3$, A' and *1 are as defined above, and $R^5$ represents an amino-protecting group; and simultaneously or sequentially removing the protecting groups to give a compound of the formula (1).

In this synthesizing route, the reduction of a compound of the formula (11) can be carried out by asymmetrically reducing method to give one of the optical isomers of a compound of the formula (10), which can be then subjected to the following steps to give one of the optical isomers of each compound of the formulae (9) and (1). These steps are characteristic of the present process.

In the aspect of the fifth synthesizing route set forth above, a compound of the formula (11), which is included within the formula (18), and a compound of the formula (10), which is included within the formula (19), are novel and are the forth and fifth preferred intermediates. The compounds do not necessarily need a column chromatography purifying step and may be used in the following reaction step after being subjected to a recrystallizing treatment and the like.

PREFERRED EMBODIMENT OF THE INVENTION

As used herein, "halogen atom" includes fluorine, chlorine, bromine and iodine, and among them, chlorine, bromine or iodine atom is generally preferred. Chlorine and bromine are particularly preferred.

$R^{21}$ and $R^2$ may be a hydrogen atom, a halogen atom or a hydroxyl group ($R^{21}$ may also be a protected hydroxyl group), with hydrogen being particularly preferred. A halogen atom is also preferred as $R^{21}$ and $R^2$. The halogen atom may be fluorine, chlorine or bromine, with chlorine and bromine being particularly preferred.

The leaving groups $B^1$ and $B^3$ may be, for example, a halogen atom or a substituted sulfonyloxy group. The halogen atom includes chlorine, bromine and iodine. The substituted sulfonyloxy group includes methanesulfonyloxy, p-toluenesulfonyloxy and trifluoromethane-sulfonyloxy and the like.

$B^2$ is a halogen atom, with chlorine, bromine and iodine being generally preferred. Chlorine and bromine are particularly preferred.

The term "lower alkyl" means a straight or branched saturated hydrocarbon containing 1 to 6 carbon atoms and may be preferably a straight or branched alkyl group, such as methyl, ethyl, n-propyl, i-propyl, n-butyl, i-butyl, sec-butyl, tert-butyl, pentyl and hexyl, or a cycloalkyl group such as cyclopropyl, cyclobutyl, cyclopentyl and cyclohexyl. Methyl is particularly preferred.

$R^1$ may be preferably the lower alkyl group as set forth above, with methyl being particularly preferred. A benzyl group may be also preferred as $R^1$.

$R^3$ and $R^4$ may be a hydrogen atom and are preferably an amino-protecting group. Examples of the amino-protecting group include, for example, an acyl group, an acyloxy group and an easily removable aralkyl group. The easily removable aralkyl group may be benzyl, substituted benzyl, naphthyl or substituted naphthyl and the like, with benzyl being particularly preferred. The aralkyl group to be used may be, for example, an aralkyl group containing 7 to 16 carbon atoms. Specific examples thereof include benzyl, phenethyl, 3-phenylpropyl, 4-phenylbutyl, (1-naphthyl)methyl, 2-(1-naphthyl)ethyl and 2-(2-naphthyl)ethyl, wherein the phenyl or naphthyl moiety may have suitable substituents such as alkyl group, alkoxy group and halogen atom on suitable positions.

The amino-protecting group $R^5$ may be, for example, an easily removable acyl or acyloxy group. The acyl or acyloxy group may be, for example, acetyl, haloacetyl, benzoyl, substituted benzoyl, tert-butoxycarbonyl, benzyloxycarbonyl or 9-fluorenylmethoxycarbonyl, with tert-butoxycarbonyl being particularly preferred.

$R^{61}$ and $R^6$ in A' and A may be a hydrogen atom, a hydroxyl group (in case of $R^{61}$, a protected hydroxyl group), an amino group (in case of $R^{61}$, a protected amino group) or an acetylamino group, with hydrogen being particularly preferred. In addition, a hydroxyl group (in case of $R^{61}$, a protected hydroxyl group) may be also preferred. *2 represents an asymmetric carbon atom and a compound containing *2 may be an optically active or racemic compound.

A carbazole group is particularly preferred as A.

Each compound of the formulae (1), (2), (7), (8), (9) and (10), in which formulae *1 means an asymmetric carbon atom, can be in the form of two optical isomers. Therefore, not only optically pure isomers of the said compounds, but also a mixture of any two isomers are encompassed in the present invention. From the viewpoint of pharmacological activity, a preferred configuration of the asymmetric carbon may be the absolute configuration R.

The hydroxyl-protecting group is not limited as long as it is commonly used as a hydroxyl-protecting group. Preferred examples of easily and selectively removable protecting group generally include, for example, a trialkylsilyl group, an alkoxyalkyl group and an acyl group. These hydroxyl-protecting groups can be introduced and removed by a known method indicated in literatures (for example, T. W. Greene, P. G. M. Wuts, et al., *Protective Groups in Organic Synthesis,* Wiley-Interscience Publication). For example, a tert-butyldimethylsilyl group (TBDMS) may be introduced into the alcohol by treating the alcohol with a sililating agent such as tert-butyldimethylchlorosilane or tert-butyldimethylsilyl trifluoromethanesulfonate in the presence of an acid scavenger. The amount of the sililating agent to be added may be generally about 1.0 to 1.5 mol for 1 mol of the alcohol. Generally, this reaction is preferably carried out in an inert medium. The inert medium may be, for example, dichloromethane, tetrahydrofuran, acetonitrile or pyridine. The inert medium may be preferably N,N-dimethylformamide. The amount of the inert medium to be used may be about 1 to 5 mL for 1 g of the alcohol. The acid scavenger may be triethylamine, N,N-diisopropylethylamine, pyridine, N,N-dimethylaminopyridine and the like. The acid scavenger may be, for example, preferably imidazole. The amount of the acid scavenger to be added may be generally about 1 to 3 mol for 1 mol of the alcohol. Generally, this reaction is preferably carried out at a temperature of about −20 to 80° C., particularly about 0° C. to room temperature, for example, for 1 to 5 hours.

A benzyloxymethyl group (BOM) may be introduced into the alcohol by treating the alcohol with chloromethyl benzyl ether in the presence of an acid scavenger. The amount of chloromethyl benzyl ether to be added may be generally about 1.0 to 1.5 mol for 1 mol of the alcohol. Generally, this reaction is preferably carried out in an inert medium. The inert medium may be tetrahydrofuran, acetonitrile, N,N-dimethylformamide and the like. The inert medium may be preferably dichloromethane. The amount of the inert medium to be used may be about 1 to 5 mL for 1 g of the alcohol. The acid scavenger may be, for example, triethylamine, pyridine or N,N-dimethylaminopyridine. The acid scavenger may be preferably N,N-diisopropylethylamine. The amount of the acid scavenger to be added may be generally about 1 to 3 mol for 1 mol of the alcohol. Generally, this reaction is preferably carried out at a temperature of about −20 to 80° C., particularly about 0° C. to room temperature, for example, for 1 to 5 hours.

In addition, an acetyl group (Ac) may be introduced into the alcohol by treating the alcohol with an acetylating agent such as acetic anhydride, acetyl chloride and the like in the presence of an acid scavenger. The amount of the acetylating agent to be added may be generally about 1 to 3 mol for 1 mol of the alcohol. Generally, this reaction is preferably carried out in an inert medium. The inert solvent may be, for example, preferably tetrahydrofuran, acetonitrile, dichloromethane or pyridine. The amount of the inert medium to be used may be about 1 to 5 mL for 1 g of the alcohol. The acid scavenger may be, for example, preferably triethylamine, N,N-diisopropylethylamine, pyridine or N,N-dimethylaminopyridine. The amount of the acid scavenger to be added may be generally about 1 to 3 mol for 1 mol of the alcohol. Generally, this reaction is preferably carried out at a temperature of about −20 to 80° C., particularly about 0° C. to room temperature, for example, for 1 to 5 hours.

The hydroxyl-protecting group can be removed as follows. For example, a tert-butyldimethylsilyl group may be removed by treating a tert-butyldimethylsilyl ether with tetrabutylammonium fluoride. The amount of tetrabutylammonium fluoride to be added may be generally about 1 to 3 mol for 1 mol of the tert-butyldimethylsilyl ether. Generally, this reaction is preferably carried out in a medium such as tetrahydrofuran. The amount of the medium to be used may be generally about 1 to 5 mL for 1 g of the alcohol. Generally, this reaction is preferably carried out at a temperature of about −20 to 60° C., particularly about 0° C. to room temperature, for example, for 1 to 5 hours. This reaction is preferably carried out in the presence of acetic acid. The amount of acetic acid to be added may be generally about 1 to 2 mol for 1 mol of the tert-butyldimethylsilyl ether.

A benzyloxymethyl group may be removed, for example, by hydrogenolysis reaction using a catalyst such as palladium/carbon or palladium hydroxide/carbon. The amount of the catalyst to be used may be generally about 5 to 20% by weight with respect to the benzyloxymethyl ether. Generally, this reaction is preferably carried out in a medium such as methanol, ethanol, tetrahydrofuran, acetic acid and the like. The amount of the medium to be used may be generally about 1 to 5 mL for 1 g of the benzyloxymethyl ether. Generally, this reaction is preferably carried out at a temperature of about −10 to 50° C., particularly at room temperature, for example, for 3 to 10 hours.

An acetyl group may be removed by subjecting an acetic ester to hydrolysis reaction using a base such as sodium carbonate, potassium carbonate, sodium hydroxide, potassium hydroxide and the like. The amount of the base to be added may be generally about 0.1 to 10 mol for 1 mol of the acetic ester. Generally, this reaction is preferably carried out in a medium such as methanol, ethanol, tetrahydrofuran or 1,4-dioxane, or a water-mixed medium thereof. The amount of the medium to be used may be generally about 1 to 5 mL for 1 g of the acetic ester.

Generally, this reaction is preferably carried out at a temperature of about −20 to 100° C., particularly about 0 to 50° C., for example, for 1 to 5 hours.

In accordance with the present invention, a compound having the hydroxyl group attached to the asymmetric carbon atom *1, which is derived from the reduction of the corresponding carbonyl group, can be used in the following reactions without protection of the hydroxyl group. It is preferred, however, that such a compound is used after being protected with a suitable protecting group as occasion requires.

The amino-protecting group can be removed by a known method indicated in literatures (for example, T. W. Greene, P. G. M. Wuts, et al., *Protective Groups in Organic Synthesis,* Wiley-Interscience Publication). For example, a benzyl group may be removed by hydrogenolysis reaction using a catalyst such as palladium/carbon or palladium hydroxide/carbon. The amount of the catalyst to be used may be generally about 5 to 20% by weight with respect to the protected amine. Generally, this reaction is preferably carried out in a medium such as methanol, ethanol, tetrahydrofuran, acetic acid and the like. The amount of the medium to be used may be generally about 1 to 5 mL for 1 g of the protected amine. Generally, this reaction is preferably carried out at a temperature of about −10 to 50° C., particularly at room temperature, for example, for 3 to 10 hours. When $R^{21}$ is a halogen atom, however, the amino-protecting group is removed by a known method indicated in the literatures (M. Koreeda et al., *Journal of Organic Chemistry,* 49, p. 2081 (1984) and S. Gubert et al., *Synthesis,* 4, p. 318 (1991)).

An acetyl group may be removed according to the acetic ester-hydrolyzing process using basic condition as set forth above. When an acyl group is used as the amino-protecting group, however, it may be preferred that this hydrolysis reaction is generally carried out at a temperature of room temperature to about 100° C.

A tert-butoxycarbonyl group (Boc) may be removed by reacting the corresponding protected amine with a known mineral acid or Lewis acid. The known mineral acid or Lewis acid may be hydrochloric acid, hydrobromic acid, sulfuric acid, acetic acid, trifluoroacetic acid, aluminum chloride, bromotrimethylsilane, iodotrimethylsilane and the like, with hydrochloric acid being preferred. The amount of the mineral acid or Lewis acid to be added may generally vary from about the same molar amount with respect to the protected amine to a solvent amount with respect to the protected amine. This reaction can be carried out in a medium. However, this reaction may also be preferably carried out using the above acid as a medium. The medium may be a lower alcohol such as methanol, ethanol and n-propanol, 1,4-dioxane, tetrahydrofuran, acetonitrile, dichloromethane and the like, with methanol and ethanol being preferred. Generally, this reaction is preferably carried out at a temperature of about −30 to 100° C., particularly about 0° C. to room temperature, for example, for 1 to 10 hours.

The hydroxyl- and amino-protecting groups may be sequentially or simultaneously removed. For example, when $R^{21}$ is a benzyloxy group, $R^3$ is a benzyl group and $R^4$ is a benzyl or benzyloxycarbonyl group respectively, they can be removed under the same reaction condition and are preferably simultaneously removed. When $R^{21}$ is a benzyloxy group and $R^4$ is a tert-butoxycarbonyl group respectively, they can be removed by sequential steps comprising, for example, the first removal of the tert-butoxycarbonyl group as $R^4$ followed by the removal of the benzyloxy group as $R^{21}$. The sequence of removal is not limit to the above and is preferably selected depending on the physical properties of the compound to be deprotected. The condition for removing each protecting group is as set forth above. In addition, these deprotection can be carried out with reference to the teachings of JP-A-9-249623.

Examples of a compound represented by the formula (1) include

2-[N-[2-(9H-carbazol-2-yloxy)]ethyl]amino-1-(3-methylsulfonylamino)phenylethanol;
2-[N-[2-(9H-carbazol-2-yloxy)]ethyl]amino-1-(4-hydroxy-3-methylsulfonylamino)phenylethanol;
2-[N-[2-(9H-carbazol-2-yloxy)]ethyl]amino-1-(4-bromo-3-methylsulfonylamino)phenylethanol;
2-[N-[2-(9H-carbazol-2-yloxy)]ethyl]amino-1-(4-chloro-3-methylsulfonylamino)phenylethanol; and
2-[N-[2-(6-hydroxy-9H-carbazol-2-yloxy)]ethyl]amino-1-(3-methylsulfonylamino)phenylethanol.

The most preferred examples are the above-mentioned compounds in the R-form.

The processes for the preparation of a compound represented by the formula (1) according to the present invention are illustrated in more detail in the followings.

[Preparing Process 1]

A compound of the formula (4) is condensed with a compound of the formula (12) to give a compound of the formula (3), which is then reduced to give an amino-alcohol of the formula (2). At the final step, the protecting groups are simultaneously or sequentially removed to give a compound of the formula (1).

A compound represented by the formula (4) is a known compound and can be synthesized by the method indicated in the literature (A. A. Larsen et al., *J. Med. Chem.*, 10, p. 462 (1967), or C. Kaiser et al., *J. Med. Chem.*, 7, p. 49 (1974)).

A compound represented by the formula (3), which is a novel compound and is relatively good in crystallinity, is characteristic of the present process as an important intermediate. The recrystallizing step can be carried out by a commonly applicable means, which may be preferably a means comprising dissolving a compound of the formula (3) in a lower alcohol such as methanol or ethanol, followed by cooling to allow the compound to crystallize.

A compound represented by the formula (3) can be obtained by reacting a compound of the formula (4) with a compound of the formula (12). The amount of the compound of the formula (12) to be added may be about 0.9 to 5 mol for 1 mol of the compound of the formula (4). Generally, this reaction is preferably carried out in an inert medium. The inert medium may be, for example, acetonitrile, acetone, methyl ethyl ketone, methanol, ethanol, tetrahydrofuran or dichloromethane, with tetrahydrofuran being preferred. The amount of the inert medium to be used may be generally about 1 to 100 mL for 1 g of the compound of the formula (4).

Generally, this reaction is preferably carried out at a temperature of about −20° C. to 100° C., particularly about 0 to 50° C., for example, for 3 to 10 hours. This reaction is also preferably carried out in the presence of a base as an acid scavenger. As the base, a tertiary amine or an inorganic base can be used. The tertiary amine may be, for example, triethylamine, N,N-diisopropylethylamine or N,N-dimethylaminopyridine. The inorganic base may be, for example, potassium carbonate or potassium hydrogen carbonate. The amount of the acid scavenger to be used may be generally 1 to 5 mol for 1 mol of the compound of the formula (4).

A compound represented by the formula (12) can be obtained by protecting a primary amine which is a known compound represented by the formula:

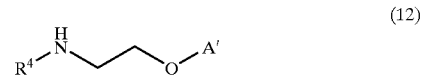

(12)

(synthesized by the known method indicated in JP-A-9-249623) with a protecting group $R^4$. That is, when $R^4$ is a benzyl group, the protecting step can be carried out by reductive alkylation reaction with benzaldehyde, or by alkylation reaction with benzyl halide, benzyl sulfonate and the like. For example, the amount of benzaldehyde to be added according to the reductive alkylation reaction may be generally about 1 to 1.5 mol for 1 mol of the compound of the formula (12). Generally, this reaction is preferably carried out in a medium such as tetrahydrofuran, water, methanol or ethanol. Methanol may be most preferably used as the medium. The amount of the medium to be used may be generally about 10 to 100 mL for 1 g of the compound of the formula (12). Generally, this reaction is preferably carried out at room temperature, for example, for 3 to 10 hours. Further, it is also preferred that this reaction is generally carried out in the presence of a platinum group metal-comprising catalyst. The platinum group metal-comprising catalyst may be preferably platinum oxide. The amount of the platinum group metal-comprising catalyst to be used may be generally about 0.01 to 0.1 mol for 1 mol of the compound of the formula (12). This reaction is to be carried out under a hydrogen atmosphere. Generally, it may be preferably carried out at a pressure of about 1 to 10 atm, particularly preferably about 1 to 3 atm.

Alternatively, a compound represented by the formula (12) may be synthesized from a compound represented by A'—OH by a process consisting of 2 steps. That is, a compound of the formula (12) can be obtained by reacting a known compound of A'—OH with 1,2-dibromoethane to give the corresponding brominated compound, followed by reacting with an amine ($NH_2$—$R^4$)(in case that $R^4$ is a substituted benzyl group).

The reaction between a compound represented by A'—OH and 1,2-dibromoethane may be carried out in an organic solvent, generally in the presence of a base at a temperature of room temperature to the reflux temperature of the thus selected solvent. The amount of 1,2-dibromoethane to be used is preferably 3 to 15 mol for 1 mol of the compound of A'—OH. The solvent may be dimethylformamide, dimethylacetamide, 2-butanone, acetonitrile, diglyme or tetrahydrofuran. The base may be potassium carbonate, sodium carbonate, sodium hydroxide, potassium hydroxide, triethylamine, pyridine, sodium hydride, sodium methoxide and the like, which is preferably used at an amount of 1 to 5 mol for 1 mol of the compound of A'—OH. The amount of the medium to be used is generally about 5 to 100 mL for 1 g of the compound of A'—OH. Generally, this reaction is preferably carried out at a temperature of 60 to 90° C., for example, for 3 to 24 hours.

The reaction of the brominated compound with $NH_2$—$R^4$ may be carried out in a solvent or without solvent at a temperature of 60 to 100° C. The amount of $NH_2$—$R^4$ to be used may be 2 to 10 mol for 1 mol of the brominated compound. The solvent may be dimethylformamide, dimethylacetamide, dimethylsulfoxide, 2-propanol and the like.

A compound represented by the formula (2) can be obtained by reducing a compound represented by the formula (3) with a known reducing agent. The reducing agent may be, for example, sodium borohydride, borane or diisobutylaluminum hydride. The reducing reaction may be preferably carried out with a metal hydride such as sodium borohydride, or with hydrogen in the presence of a platinum group metal-comprising catalyst such as palladium catalyst. The amount of sodium borohydride to be added may be generally about 1 to 3 mol for 1 mol of the compound of the formula (3). Generally, this reaction is preferably carried out in a lower alcohol. The lower alcohol may be, for example, methanol or i-propanol, and is preferably ethanol. The amount of the lower alcohol to be used may be generally about 1 to 5 mL for 1 g of the compound of the formula (3). However, when the solubility is insufficient, it may be preferred that tetrahydrofuran as a cosolvent is generally added in an amount of about 1 to 5 mL for 1 g of the compound of the formula (3). Generally, this reaction is preferably carried out at a temperature of about −20 to 50° C., particularly about 0° C. to room temperature, for example, for 1 to 5 hours.

In addition, if an optical isomer of either R-form or S-form with respect to *1 of the formula (2) is to be obtained, it can be obtained by asymmetric reduction in the presence of an asymmetric reduction catalyst known from a variety of literatures (for example, Achiwa et al. *Chem. Pharm., Bull.*, 43, p. 748 (1995) or Nozaki et al. *J. Org. Chem.*, 59, pp. 3064–3076 (1994).

The method of Nozaki et al. is concerned with an asymmetric reduction with respect to 1,1-dimethylaminoacetone, in which method a cationic ruthenium-BINAP(2,2'-bis (diphenylphosphino)-1,1'-binaphthyl) complex of [RuI((S)-BINAP)(p-cymene)]$^+$ I$^-$ is used, and this method may also be preferred for the present invention.

Further, WO 97/20789 and JP-A-9-157196 each teach a variety of processes for the preparation of an optically active alcohol from a ketone compound. Such processes use a metal complex comprising a transition metal with various ligands, more preferably, for example, a transition metal complex which may be represented by $MX_mL_n$ wherein M represents a transition metal of the VIII group such as iron, cobalt, nickel, ruthenium, rhodium, iridium, osmium, palladium or platinum; X represents a hydrogen atom, a halogen atom, a carboxyl group, a hydroxyl group or an alkoxyl group; L represents a neutral ligand such as an aromatic compound or an olefin compound; m and n represent an integer. Ruthenium is a preferred transition metal to be contained in such transition metal complexes. When the neutral ligand is an aromatic compound, it may be a monocyclic aromatic compound. The aromatic compound may be substituted with various substituents such as a hydrogen atom, a saturated or unsaturated hydrocarbon group, an allyl group or a functional group containing heteroatom(s), at any positions of the aromatic compound, and the number of the substituents is not limited. The substituents may be specifically an alkyl group such as methyl, ethyl, propyl, i-propyl, butyl, tert-butyl, pentyl, hexyl, heptyl and the like; a cycloalkyl group such as cyclopropyl, cyclobutyl, cyclopentyl, cyclohexyl and the like; an unsaturated hydrocarbon group such as benzyl, vinyl, allyl and the like; or a functional group containing heteroatom(s) such as hydroxyl group, alkoxyl group, alkoxycarbonyl group and the like.

In addition, specific examples of metal complex include the followings.

[(R,R)-N-(p-toluenesulfonyl)-1,2-diphenylethylenediamine]benzene ruthenium complex;

[(R,R)-N-(p-toluenesulfonyl)-1,2-diphenylethylenediamine](p-cymene) ruthenium complex;

[(R,R)-N-(o-toluenesulfonyl)-1,2-diphenylethylenediamine](p-cymene) ruthenium complex;

[(R,R)-N-(2-mesitylenesulfonyl)-1,2-diphenylethylenediamine](p-cymene) ruthenium complex;

((R,R)-N-methanesulfonyl-1,2-diphenylethylenediamine)(p-cymene) ruthenium complex;

((R,R)-N-benzenesulfonyl-1,2-diphenylethylenediamine)(p-cymene) ruthenium complex;

[(R,R)-N-(p-fluorobenzenesulfonyl)-1,2-diphenylethylenediamine](p-cymene) ruthenium complex;

((R,R)-N-trifluoromethanesulfonyl-1,2-diphenylethylenediamine)(p-cymene) ruthenium complex;

[(R,R)-N-(p-methoxybenzenesulfonyl)-1,2-diphenylethylenediamine](p-cymene) ruthenium complex;

((R,R)-N-methanesulfonyl-1,2-diphenylethylenediamine) mesitylene ruthenium complex;

[(R,R)-N-(p-toluenesulfonyl)-1,2-diphenylethylenediamine]mesitylene ruthenium complex;

hydride-[(R,R)-N-(p-toluenesulfonyl)-1,2-diphenylethylenediamine]benzene ruthenium complex;

hydride-[(R,R)-N-(p-toluenesulfonyl)-1,2-diphenylethylenediamine](p-cymene) ruthenium complex;

hydride-[(R,R)-N-(o-toluenesulfonyl)-1,2-diphenylethylenediamine](p-cymene) ruthenium complex;

hydride-[(R,R)-N-(2-mesitylenesulfonyl)-1,2-diphenylethylenediamine](p-cymene) ruthenium complex;

hydride-((R,R)-N-methanesulfonyl-1,2-diphenylethylenediamine)(p-cymene) ruthenium complex;

hydride-((R,R)-N-benzenesulfonyl-1,2-diphenylethylenediamine)(p-cymene) ruthenium complex;

hydride-[(R,R)-N-(p-fluorobenzenesulfonyl)-1,2-diphenylethylenediamine](p-cymene) ruthenium complex;

hydride-((R,R)-N-trifluoromethanesulfonyl-1,2-diphenylethylenediamine)(p-cymene) ruthenium complex;

hydride-[(R,R)-N-(p-methoxybenzenesulfonyl)-1,2-diphenylethylenediamine](p-cymene) ruthenium complex;

hydride-((R,R)-N-methanesulfonyl-1,2-diphenylethylenediamine)mesitylene ruthenium complex;

hydride-[(R,R)-N-(p-toluenesulfonyl)-1,2-diphenylethylenediamine]mesitylene ruthenium complex;

chloro-[(R,R)-N-(p-toluenesulfonyl)-1,2-diphenylethylenediamine]benzene ruthenium complex;

chloro-[(R,R)-N-(p-toluenesulfonyl)-1,2-diphenylethylenediamine](p-cymene) ruthenium complex;

chloro-[(R,R)-N-(o-toluenesulfonyl)-1,2-diphenylethylenediamine](p-cymene) ruthenium complex;

chloro-[(R,R)-N-(2-mesitylenesulfonyl)-1,2-diphenylethylenediamine](p-cymene) ruthenium complex;

chloro-((R,R)-N-methanesulfonyl-1,2-diphenylethylenediamine)(p-cymene) ruthenium complex;

chloro-((R,R)-N-benzenesulfonyl-1,2-diphenylethylenediamine)(p-cymene) ruthenium complex;

chloro-[(R,R)-N-(p-fluorobenzenesulfonyl)-1,2-diphenylethylenediamine](p-cymene) ruthenium complex;

chloro-((R,R)-N-trifluoromethanesulfonyl-1,2-diphenylethylenediamine](p-cymene) ruthenium complex;

chloro- [(R,R)-N-(p-methoxybenzenesulfonyl)-1,2-diphenylethylenediamine](p-cymene) ruthenium complex;

chloro-[(R,R)-N-methanesulfonyl-1,2-diphenylethylenediamine]mesitylene ruthenium complex; and chloro-[(R,R)-N-(p-toluenesulfonyl)-1,2-diphenylethylenediamine]mesitylene ruthenium complex.

Further, an asymmetric reduction using a catalyst is known, wherein the catalyst is obtained by reacting the following rhodium complex with the following chiral phosphine ligand. For example, [Rh(nbd)$_2$]ClO$_4$ (wherein nbd means norbornadiene), [Rh(nbd)Cl]$_2$, [Rh(cod)Cl]$_2$ (wherein cod means cycloocta-1,5-diene), and the like are known as a rhodium complex. Examples of chiral phosphine ligand include (2R,3R)-2,3-bis(diphenylphosphino)-bicyclo[2,2,1]hept-5-ene [abbr.: (R,R)-NORPHOS]; (R)-5,5'-dimethoxy-4,4',6,6'-tetramethyl-2-diphenylphosphino-2'-dicyclohexylphosphino-1,1'-biphenyl [abbr.: (R)-MOC-BIMOP]; (R)-5,5'-dimethoxy-4,4',6,6'-tetramethyl-2,2'-bis (dicyclohexylphosphino)-1,1'- biphenyl [abbr.: (R)-Cy-BIMOP]; (2S,3S)-1,4-bis[bis(4-methoxy-3,5-dimethylphenyl)phosphino]-2,3-(O-isopropylidene)-2,3-butanediol [abbr.: (S,S)-MOD-DIOP]; (2S,3S)-1,4-bis (diphenylphosphino)-2,3-(O-isopropylidene)-2,3-butanediol [abbr.: (S,S)-DIOP]; (2S,3S)-1-diphenylphosphino-4-dicyclohexylphosphino-2,3-(O-isopropylidene)-2,3-butanediol [abbr.: (S,S)-DIOCP]; (R)-1-[(S)-1',2-bis(diphenylphosphino)ferrocenyl]ethanol [abbr.: (R)-(S)-BPPFOH]; (S)-1-[(S)-1',2-bis (diphenylphosphino)ferrocenyl]ethanol [abbr.: (S)-(S)-BPPFOH]; (1S,2S)-1-diphenylphosphino-2-(diphenylphosphinomethyl)cyclopentane [abbr.: (S,S)-PPCP]; and (1S,2R)-1-dicyclohexylphosphino-2-(diphenylphosphinomethyl)cyclopentane [abbr.: (R,R)-CPCP].

When an asymmetric reduction according to the present invention is carried out in the presence of such a known catalyst, a suitable catalyst can be previously selected by checking the fact that the said reduction can appropriately proceed in the presence of the catalyst. However, such a checking may limit suitable catalysts, there is some possibility that appropriate catalysts to be selected is limited. Particularly preferred examples of the catalyst include those obtained by reacting a rhodium complex represented by the formula [Rh(cod)Cl]$_2$ wherein cod means cycloocta-1,5-diene, with any one of chiral phosphine represented by the formula (16):

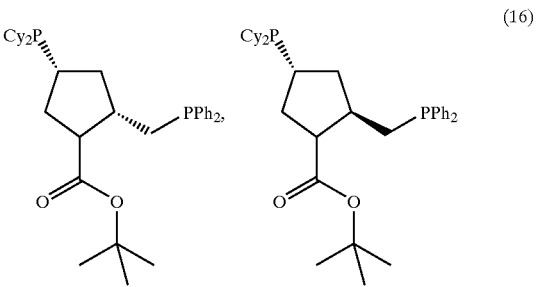

(16)

or the formula (17):

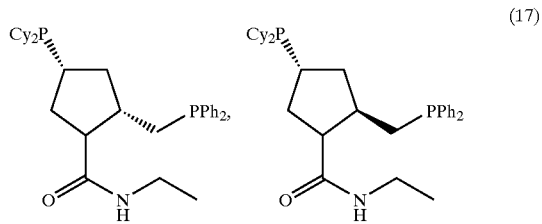

(17)

wherein Cy means a cyclohexyl group. That is, a hydrochloride compound of the formula (3) is reduced with hydrogen in the presence of the said complex [Rh(cod)Cl]$_2$ and a chiral phosphine ligand represented by the formula either (16) or (17). These reactions may be carried out according to the literature (Achiwa et al., *Chem. Pharm. Bull.*, 43, p 748 (1995)). For example, an optically active compound (amino-alcohol) represented by the formula (2) can be obtained by reducing a hydrochloride compound (ketoamine) of the formula (3) with hydrogen in the presence of a catalyst prepared from [Rh(cod)Cl]$_2$, a chiral phosphine ligand represented by the formula (16) and a base. A chiral phosphine ligand represented by the formula (16) or (17) having the conformation (2R,4R) is preferably used, when an objective compound to be obtained by asymmetric reduction is in the R-form. The amount of [Rh(cod)Cl]$_2$ to be added may be generally about $10^{-5}$ to $10^{-1}$ mol for 1 mol of the ketoamine hydrochloride. The amount of the chiral phosphine ligand represented by the formula (16) to be added may be generally about 2.6 mol for 1 mol of Rh. Examples of the base include N,N-diisopropylethylamine, sodium hydroxide, potassium hydroxide, lithium hydroxide, potassium methoxide and potassium tert-butoxide. The base may be preferably triethylamine. The amount of the base to be added may be generally about $5 \times 10^{-3}$ mol for 1 mol of the ketoamine hydrochloride. Generally, this reaction may be preferably carried out under a hydrogen atmosphere at atmospheric pressure to about 50 atm, more preferably at atmospheric pressure to about 20 atm. It is generally preferred to carry out this reaction in a medium. Examples of the medium include toluene, xylene, diethyl ether, tetrahydrofuran, 1,4-dioxane, ethanol, n-propanol, i-propanol and water. The medium may be preferably methanol. The amount of the medium to be used may be generally about 5 to 30 mL for 5 mmol of the ketoamine hydrochloride. This reaction is generally carried out at a temperature of about 0 to 100° C., preferably room temperature to about 50° C., for example, preferably for 0.5 to 2 days.

As set forth above, the ketoamine in the form of hydrochloride is more preferably used than its free form as a reactant in the present asymmetrically reducing process using a catalyst prepared from a rhodium complex.

Next, a compound of the formula (1) can be obtained by simultaneously or sequentially removing the protecting groups according to the method as set forth above.

In each step of the synthesizing route set forth above, the produced material is preferably purified by a known purifying means, such as column chromatography. However, the intermediate products such as a novel compound represented by the formula (3) are relatively good in crystallinity and can be used in the following reaction step after being subjected to a simple recrystallizing treatment without hard labor. Therefore, the present process, which can save cost and complicated process, is a preferred process. In addition, the present process is also preferred in that each step results in good yield and that the number of steps is relatively few.

[Preparing Process 2]

A compound of the above-mentioned general formula (3) may be synthesized by either process as set forth below. That is, a compound of the formula (3) can be obtained by condensing a compound of the formula (4) with a compound of the formula (14) to give a compound of the formula (6); and converting its hydroxyl group into a leaving group $B^3$ to give a compound of the formula (5), which is then condensed with a compound represented by A'—OH.

The condensation of a compound of the formula (4) with a compound of the formula (14) can be carried out under the same reaction conditions with those of the reaction of a compound of the formula (4) with a compound of the formula (12) according to the Preparing Process 1 as set forth above. In this connection, $R^4$ in the formula (14) and $R^4$ in the formula (12), which are common in that they are an amino-protecting group, do not necessarily mean the same group and may be different from each other.

A compound represented by the formula (6) obtained by the condensation of a compound of the formula (4) with a compound of the formula (14) is novel and is a preferred intermediate. The compound does not necessarily need a column chromatography purifying step and may be used in the following reaction step after being subjected to a recrystallizing treatment and the like.

Among compounds represented by the formula (14), which can be synthesized by the same reaction conditions with those of Referential Examples of the present text of specification, a compound of the formula (14) in which $R^4$ is a benzyl group is commercially available (mfd. by TOKYO KASEI KOGYO) and is particularly preferred.

A compound represented by the formula (5) can be obtained by converting the hydroxyl group (the primary hydroxyl group) of the side-chain of a compound of the formula (6) to a leaving group $B^3$. The conversion into a leaving group $B^3$ may be carried by halogenation with a known halogenating agent such as hydrogen bromide/acetic acid, phosphorus tribromide, phosphorus pentabromide, phosphorus trichloride, phosphorus pentachloride, phosphorus oxychloride, thionyl chloride, thionyl bromide, bromine/triphenylphosphine, carbon tetrachloride/triphenylphosphine, carbon tetrabromide/triphenylphosphine, N-bromosuccinimide/triphenylphosphine and the like, or by sulfonic esterification with a sulfonyl chloride such as methanesulfonyl chloride, p-toluenesulfonyl chloride and the like. For example, a compound of the formula (5) in which $B^3$ is bromine may be obtained by treating a compound of the formula (6) with about 1- to 10-fold moles of phosphorus tribromide. Generally, this reaction is preferably carried out in an inert medium. The inert medium may be, for example, 1,2-dichloroethane or carbon tetrachloride, and is preferably dichloromethane. The amount of the inert medium to be used may be generally about 1 to 10 mL for 1 g of the compound of the formula (6). This reaction is generally carried out at a temperature of about −30 to 100° C., particularly about 0 to 50° C., for example, preferably for 1 to 5 hours. In addition, a methanesulfonate ester may be generally obtained by treating a compound of the formula (6) with about 1- to 3-fold moles of methanesulfonic chloride. Generally, this reaction is preferably carried out in an inert medium. The inert medium may be, for example, dichloromethane, tetrahydrofuran or toluene, and is preferably pyridine. The amount of the inert medium to be used may be generally about 1 to 10 mL for 1 g of the compound of the formula (6). This reaction is generally carried out at a temperature of about −20 to 100° C., preferably about 0 to 50° C., for example, preferably for about 1 to 5 hours. This reaction may be also preferably carried out in the presence of a tertiary amine such as triethylamine, N,N-diisopropylethylamine, N,N-dimethylaminopyridine and the like. The amount of the tertiary amine to be used may be about 1- to 5-fold moles.

As obtained sulfonate ester compound may be directly subjected to the following condensation reaction with a compound represented by A'—OH, or may be first halogenated with a halogenating agent such as sodium chloride, sodium bromide, sodium iodide, potassium bromide or potassium iodide by a known method (for example, *Org. Syn. Coll. Vol.*, 4, p. 753 (1963)) followed by condensation with a compound represented by A'—OH. Generally, the iodide may be obtained by treating the corresponding sulfonate ester with about 1- to 10-fold moles of sodium iodide. Generally, this reaction is preferably carried out in an inert medium. The inert medium may be, for example, 2-butanone, tetrahydrofuran, N,N-dimethylformamide, N,N-dimethylacetamide, dimethylsulfoxide or sulfolane, and is preferably acetone. The amount of the inert medium to be used may be generally about 1 to 10 mL for 1 g of the sulfonate ester. This reaction is generally carried out at a temperature of about 0 to 150° C., preferably about room temperature to about 100° C., for example, preferably for 3 to 10 hours.

Generally, the condensation reaction of a compound of the formula (5) with a compound represented by A'—OH is preferably carried out by reacting 1 to 5 mol of the compound of A'—OH for 1 mol of the compound of the formula (5) in a basic condition. The basic condition preferably comprises treatment with an alkali such as potassium carbonate, potassium hydroxide, sodium hydroxide, sodium hydride, potassium hydride and potassium tert-butoxide. In this basic condition the compound of A'—OH is formed into the metal alkoxide by each alkali. The amount of the metal alkoxide to be used may be generally about 1 to 3 mol for 1 mol of the halide or sulfonic ester. Generally, this reaction is preferably carried out in an inert medium. The inert medium may be, for example, acetone, 2-butanone, tetrahydrofuran, N,N-dimethylacetamide, dimethylsulfoxide or sulfolane, and is preferably N,N-dimethylformamide. The amount of the inert medium to be used may be generally about 1 to 10 mL for 1 g of the sulfonic ester. Generally, this reaction is preferably carried out at a temperature of room temperature to about 100° C., for example, for 3 to 10 hours.

In addition, a ketoamine represented by the formula (3) may be obtained by directly condensing a compound of the formula (6) with a compound represented by A'—OH according to Mitsunobu reaction. The reaction can be carried out in accordance with the method indicated in literatures (for example, Mitsunobu et al. *Journal of Organic Chemistry*, 50, p. 3095 (1985)). For example, a compound of the formula (6) may be reacted with 1- to 2-fold moles of a compound of A'—OH in the presence of 1- to 2-fold moles of a condensing agent prepared from a trivalent organophosphorus compound, such as triphenylphosphine, triethylphosphine, triethylphosphine and the like, and an azo compound such as diethyl azodicarboxylate (DEAD), N,N,N',N'-tetramethyl-azodicarboxamide (TMAD), 1,1-(azodicarbonyl)dipiperidine (ADDP), cyanomethylenetributyl phosphorane (CMBP) or cyanomethylenetrimethyl phosphorane (CMMP), phosphorane and the like. Generally, this reaction is preferably carried out in an inert medium. The inert medium may be benzene or toluene, and is preferably tetrahydrofuran. The amount of the inert medium to be used may be generally about 1 to 10 mL for 1 g of the compound of the formula (6). This reaction is generally carried out at a temperature of about 0 to 100° C., preferably about 0 to 50° C., most preferably room temperature to 50° C., for example, preferably for 3 to 10 hours.

A compound represented by A'—OH can be obtained by the methods disclosed in JP-A-9-249623 (WO 97/25311) and WO 99/01431. However, 2-hydroxycarbazole is commercially available (mfd. by Aldrich) and such commercially available products are easily used and preferred.

The thus obtained compound of the formula (3) can be subjected to the following synthesizing steps in accordance with the same conditions with those of the Preparing Process 1 as set forth above to give each of a compound of the formula (2) and a compound of the formula (1).

In each step of the synthesizing route set forth above, the produced material is preferably purified by a known purifying means, such as column chromatography. However, the intermediate products such as a novel compound represented by the formula (3) are relatively good in crystallinity and can be used in the following reaction step after being subjected to a simple recrystallizing treatment without hard labor. Therefore, the present process, which can save cost and labor, is a preferred process. In addition, the present process is also preferred in that each step results in good yield and that the number of steps is relatively few.

[Preparing Process 3]

A compound of the above-mentioned general formula (2) may be also synthesized by a process set forth below. That is, an amino-alcohol represented by the formula (2) can be obtained by reducing the carbonyl group of a compound of the formula (5) to give a compound of the formula (7), followed by condensation with a compound represented by A'—OH.

The reaction for reducing or asymmetrically reducing a compound of the formula (5) can be carried out under the same reaction conditions with those of the process for synthesizing a compound of the formula (2) from a compound of the formula (3) set forth above (Preparing Process 1).

The condensation reaction of a compound of the formula (7) with a compound represented by A'—OH can be carried out under the same reaction conditions with those of the process for synthesizing a compound of the formula (3) from a compound of the formula (5) as set forth above (Preparing Process 2). For example, the condensation reaction is preferably carried out in a basic condition.

The thus obtained compound of the formula (2) can be subjected to the following synthesizing steps in accordance with the same conditions with those of the Preparing Process 1 set forth above to give a compound of the formula (1).

In each step of the synthesizing route set forth above, the produced material is preferably purified by a known purifying means, such as column chromatography. However, the intermediate products such as a novel compound represented by the formula (6) do not necessarily need a purifying step and can be used in the following reaction step after being subjected to a simple treatment, such as a recrystallizing treatment. Therefore, the present process, which can save cost and labor, is a preferred process. In addition, the present process is also preferred in that each step results in good yield and that the number of steps is relatively few.

[Preparing Process 4]

A compound of the formula (2) may be also synthesized by either process set forth below. That is, a compound represented by the above-mentioned general formula (6) is reduced (or asymmetrically reduced) to give a compound of the formula (8). Next, (i) the primary hydroxyl group of the compound of the formula (8) can be converted into a leaving group $B^3$ to give a compound of the formula (7), which can be then condensed with a compound represented by A'—OH in accordance with the Preparing Process 3 set forth above to give a compound of the formula (2).

Alternatively, (ii) the compound of the formula (8) can be subjected to Mitsunobu reaction with a compound represented by A'—OH to give a compound of the formula (2).

The reaction for reducing or asymmetrically reducing a compound of the formula (6) can be carried out under the same reaction conditions with those of the process for synthesizing a compound of the formula (2) from a compound of the formula (3) as set forth above (Preparing Process 1).

A compound represented by the formula (8) obtained by the reduction (or asymmetric reduction) of a compound of the formula (6) is novel and is a preferred intermediate. The compound does not necessarily need a purifying step and may be used in the following reaction step after being subjected to a simple treatment, such as a recrystallizing treatment. Therefore, the present process using the said compound can save cost and labor.

A compound represented by the formula (7) can be obtained by treating the primary hydroxyl group of a compound of the formula (8) in accordance with the same methods with those for preparing a compound of the formula (5) from a compound of the formula (6) as set forth above (Preparing Process 2).

The step of directly condensing a compound of the formula (8) with a compound represented by A'—OH according to Mitsunobu reaction to give a compound of the formula (2), can be carried out by reacting a compound of the formula (8) with a compound represented by A'—OH in the presence of a trivalent organophosphorus compound and an azo compound or phosphorane as a condensing agent as set forth above (Preparing Process 2).

The thus obtained compound of the formula (2) can be treated under the same conditions with those of the Preparing Process 1 as set forth above to give a compound of the formula (1).

In each step of the synthesizing route set forth above, the produced material is preferably purified by a known purifying means, such as column chromatography. However, compounds represented by the formulae (6) and (8), which are novel compounds, do not necessarily need a purifying step and may be used in the following reaction step after being subjected to a simple treatment, such as a recrystallizing treatment. Therefore, these compounds are preferred intermediates which can save cost and labor. In addition, the present process is also preferred in that each step results in good yield and that the number of steps is relatively few.

[Preparing Process 5]

A compound of the formula (4) is condensed with a compound of the formula (13) to give a compound of the formula (11), the carbonyl group of which is then reduced to give a compound of the formula (10). After the amino groups are protected, the compound of the formula (10) is condensed with a compound represented by A'—OH to give a compound of the formula (9). The amino-protecting groups can be simultaneously or sequentially removed to give a compound of the formula (1).

A compound of the formula (11) can be obtained by treating a compound of the formula (4) with a compound of the formula (13). The amount of the compound of the formula (13) to be added may be generally about 1 to 5 mol for 1 mol of the compound of the formula (4). Generally, this reaction is preferably carried out in the presence of an acid scavenger. The acid scavenger may be, for example, a tertiary amine such as triethylamine or N,N-diisopropylethylamine, potassium hydroxide, sodium carbonate or sodium hydrogencarbonate, and is preferably sodium hydroxide. The amount of the acid scavenger to be added may be generally about 2 to 10 mol for 1 mol of the compound of the formula (4). Generally, this reaction is preferably carried out in a lower alcohol such as methanol, ethanol or i-propanol, tetrahydrofuran or 1,4-dioxane, or a water-mixed medium thereof. The amount of the medium to be used is generally about 1 to 5 mL for 1 g of the compound of the formula (4). Generally, this reaction is preferably carried out at a temperature of about 0 to 100° C., particularly about 0 to 50° C., for example, preferably for 3 to 10 hours.

A compound of the formula (13) in which $B^1$ and $B^2$ are chlorine or bromine is commercially available (mfd. by TOKYO KASEI KOGYO) and such commercially available products are easily used and preferred.

The reaction for reducing or asymmetrically reducing the carbonyl group of a compound of the formula (11) can be carried out under the same reaction conditions with those of the process for synthesizing a compound of the formula (2) from a compound of the formula (3) as set forth above (Preparing Process 1).

The amino group of a compound of the formula (10) can be protected with a protecting group $R^5$ in accordance with a known method. For example, when $R^5$ is a tert-butoxycarbonyl group, a compound of the formula (10) in which the amino group is protected with $R^5$ can be obtained by treating the compound with di-tert-butyl dicarbonate in the presence of an acid scavenger. The acid scavenger may be preferably triethylamine, N,N-diisopropylethylamine, sodium hydroxide, potassium hydroxide, sodium carbonate, potassium carbonate, sodium hydrogencarbonate and the like. Generally, the amount of the acid scavenger to be added may be preferably about 1 to 3 mol for 1 mol of the compound (amino-alcohol hydrochloride) of the formula (10). Generally, this reaction is preferably carried out in a medium. The medium may be preferably a lower alcohol such as methanol, ethanol, n-propanol, i-propanol or tert-butanol, 1,4-dioxane or tetrahydrofuran, or a water-mixed medium thereof. The amount of the medium to be used is generally about 1 to 10 mL for 1 g of the amino-alcohol hydrochloride of the formula (10). Generally, this reaction is preferably carried out at a temperature of about −20 to 80° C., particularly about 0 to 50° C., most preferably about 0° C. to room temperature, for example, preferably for 1 to 10 hours.

The amino-protecting groups of a compound of the formula (9) can be simultaneously or sequentially removed in accordance with a known method to give a compound of the formula (1).

In each step of the synthesizing route set forth above, the produced material is preferably purified by a known purifying means, such as column chromatography. However, each intermediate, particularly, a compound of the formula (11), which is included within the formula (18), and a compound of the formula (10), which is included within the formula (19), do not necessarily need a purifying step and may be used in the following reaction step after being subjected to a simple treatment, such as a recrystallizing treatment. The present process, which can save cost and labor, is a preferred process. In addition, the present process is also preferred in that each step results in good yield and that the number of steps is relatively few.

The step for asymmetrically reducing a carbonyl group according to Preparing Processes 1 to 5 set forth above, is characteristic of the present invention and is a particularly preferred step in each Preparing Process.

Preferred intermediates to be used in the preparing processes of the present invention include compounds represented by the following general formula (18) and salts thereof:

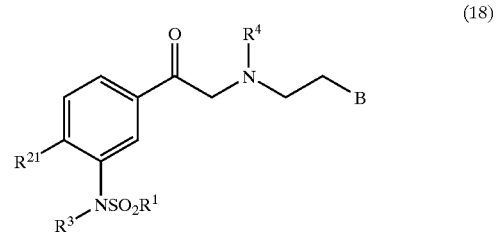

(18)

wherein $R^1$ represents a lower alkyl group or a benzyl group; $R^{21}$ represents a hydrogen atom, a halogen atom, a hydroxyl group or a protected hydroxyl group; $R^3$ represents an amino-protecting group or a hydrogen atom; $R^4$ represents an amino-protecting group or a hydrogen atom; and B represents a hydroxyl group or a leaving group. The aforementioned general formulae (5), (6) and (11) are included within the formula (18). Compounds of the formula (18) are preferred compounds which are good in crystallinity.

The other preferred intermediates include compounds represented by the following general formula (19) and salts thereof:

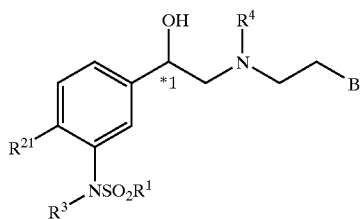

(19)

wherein $R^1$ represents a lower alkyl group or a benzyl group; $R^{21}$ represents a hydrogen atom, a halogen atom, a hydroxyl group or a protected hydroxyl group; $R^3$ represents a hydrogen atom or an amino-protecting group; $R^4$ represents an amino-protecting group or a hydrogen atom; B represents a hydroxyl group or a leaving group; and *1 represents an asymmetric carbon atom. The aforementioned general formulae (7), (8) and (10) are included within the formula (19).

As set forth above, a compound of the formula (1) in which $R^6$ is a hydrogen atom can exist in the two different optically active substances. The processes described herein can provide a racemic mixture and also an optical isomer as occasion requires. The reactions set forth above should not alter the relating stereochemistry.

When $R^6$ is a hydrogen atom, a mixture of two optical isomers with respect to *1 may be obtained. The mixture can be resolved into the optical isomers as their acid addition salts with an optically active acid such as camphorsulfonic acid, mandelic acid or substituted mandelic acid by a suitable method such as fractional crystallization. Such a fractional crystallization may be carried out using a suitable solvent, preferably a lower alcohol, such as methanol, ethanol, i-propanol or a mixture thereof. Each pair of enantiomers can be resolved into pure isomers by formation of diastereomeric salt, chromatography using an optically active column, or other means. When one of starting materials is optically active, the thus obtained mixture of diastereomers can be resolved into pure isomers by the above-mentioned means. Not only a compound of the formula (1) but also an intermediate amino-alcohol (2), (7), (8), (9) or (10) each obtained in the intermediate steps of the Preparing Processes 1 to 5 set forth above can be subjected to the said resolution. Optical resolution and purification of the present compounds can provide a preferred medicine which comprises a single isomer having higher activities and thereby has improved efficacy with little side effect.

Salts of a compound of the formula (1), (2), (3), (5), (6), (7), (8), (9), (10), (11), (18) or (19) according to the present invention may be a known salt, and examples thereof include hydrochloride, hydrobromide, sulfate, hydrogensulfate, dihydrogen phosphate, citrate, maleate, tartrate, fumarate, gluconate and methanesulfonate, and acid addition salts with an optically active acid such as camphorsulfonic acid, mandelic acid or substituted mandelic acid. Among them, pharmaceutically acceptable salts are particularly preferred. When a compound of the formula (1), (2), (3), (5), (6), (7), (8), (9), (10), (11), (18) or (19) is converted into its salt, an acid addition salt of the compound can be obtained by dissolving the compound in an alcohol such as methanol or ethanol, to which the equivalent amount to several times amount of the acid is then added. The acid to be used may be a pharmaceutically acceptable mineral or organic acid, such as hydrochloric acid, hydrobromic acid, sulfuric acid, hydrogensulfate, dihydrogen phosphate, citric acid, maleic acid, tartaric acid, fumaric acid, gluconic acid, methanesulfonic acid and the like.

This specification includes part or all of the contents as disclosed in the specification of Japanese Patent Application No. 11-83917.

EXAMPLES

The following examples further illustrate this invention but are not intended to limit it in any way.

The thin layer chromatography (TLC) used was Precoated silica gel 60 F254 (mfd. by Merck). After developing with chloroform/methanol (1:0 to 4:1), chloroform/acetone (1:0 to 10:1) or n-hexane/ethyl acetate (1:0 to 1:10), the detecting process was carried out with UV (254 nm) irradiation and coloration with ninhydrin. $R_f$ values of TLC were obtained on free amines. The column chromatography process was carried out on silica gel 60 (230–400 mesh; mfd. by Merck). The determination of nuclear magnetic resonance spectrum (NMR) was carried out using Gemini-300 (FT-NMR; mfd. by Varian). Mass spectrum (MS) was determined by the fast atom bombardment mass spectrometry (FAB-MS) with JEOL-JMS-SX102.

Referential Example 1

Synthesis of N-benzyl-N-[2-(9H-carbazol-2-yloxy)] ethylamine

Benzaldehyde (9.38 g) was added to a solution of N-[2-(9H-carbazol-2-yloxy)]ethylamine (20 g; synthesized according to the process indicated in JP-A-9-249623) in methanol (500 mL). The mixture was then stirred at room temperature for 1 hour. Under an argon atmosphere, platinum oxide (1.00 g; mfd. by Wako Pure Chemical Industries) was added to the mixture, which was then stirred under a hydrogen atmosphere at atmospheric pressure for 3 hours. After replacing the atmosphere in the reaction system with argon, benzaldehyde (1.88 g) was added to the mixture, which was then further stirred under a hydrogen atmosphere at atmospheric pressure for 3 hours. After replacing the atmosphere with argon, the catalyst was filtered off and the solvent was distilled off under reduced pressure. The residue was recrystallized from ethanol and dried under reduced pressure to give the title compound (25.2 g) as a pale yellow crystal.

$R_f$: 0.6 (10:1 chloroform/methanol).

$MH^+$: 317.

$^1$H-NMR (DMSO-$d_6$; free form): 2.30 (1H, s), 2.91 (2H, t, J=5.8), 3.79 (2H, s), 4.11 (2H, t, J=5.8), 6.77 (1H, dd, J=8.5, 2.2), 6.96 (1H, d, J=2.2), 7.10 (1H, m), 7.20–7.44 (7H, m), 7.92–8.00 (2H, m), 11.09 (1H, s).

Referential Example 2

Alternative Synthesis of N-benzyl-N-[2-(9H-carbazol-2-yloxy)ethyl]amine

Step A. Synthesis of 2-(2-bromoethoxy)carbazole

A mixture of 2-hydroxycarbazole (30 g; mfd. by Aldrich), potassium carbonate (113.1 g; mfd. by KANTO CHEMICAL) and 1,2-dibromoethane (211 mL; mfd. by TOKYO KASEI KOGYO) in 2-butanone (165 mL; mfd. by Wako Pure Chemical Industries) was stirred vigorously at a reflux temperature for 28 hours. The reaction solution was poured into water (1050 mL) all at once and stirred. The precipitated crystal obtained by filtration was washed with water (1 L) and 2-propanol (250 mL), and then dried under reduced pressure at room temperature to give the title compound (43.43 g) as a white solid.

$R_f$: 0.51 (1:2 ethyl acetate/n-hexane).

$^1$H-NMR (DMSO-$d_6$): 3.82–3.85 (2H, m), 4.36–4.43 (2H, m), 6.80 (1H, dd, J=8.5, 2.2), 6.99 (1H, d, J=2.2), 7.11 (1H, m), 7.29 (1H, m), 7.42 (1H, d, J=8.3), 7.98 (1H, d, J=8.5), 8.00 (1H, d, J=7.7), 11.13 (1H, s).

Step B. Synthesis of N-benzyl-N-[2-(9H-carbazol-2-yloxy)ethyl]amine

A mixture of the compound (80 g; obtained from the step A above) in benzyl amine (270 mL; mfd. by TOKYO KASEI KOGYO) was stirred with heating at an internal temperature of 100° C. for 4 hours. The reaction solution was poured into water (2.3 L) all at once and stirred for 30 minutes. The precipitated crystal obtained by filtration was then washed with water (1.5 L) and 2-propanol (1 L), and dried under reduced pressure at room temperature to give the title compound (76.5 g).

$R_f$: 0.33 (1:2 ethyl acetate/n-hexane).

The thus obtained compound showed the same NMR data with those of the compound of Referential Example 1.

Example 1

Synthesis of 2-[N-benzyl-N-[2-(9H-carbazol-2-yloxy)]ethyl]amino-1-(3-methylsulfonylamino)phenylethanone Hydrochloride (Preparing Process 1)

A solution of 2-bromo-1-(3-methylsulfonylamino)phenylethanone (10 g; prepared according to the method reported by A. A. Larsen et al., *J. Med. Chem.*, 10, p. 462 (1967)) in tetrahydrofuran (100 mL) was added dropwise to a solution of N-benzyl-N-[2-(9H-carbazol-2-yloxy)]ethylamine (21.7 g; obtained from Referential Example) in tetrahydrofuran (100 mL), followed by stirring overnight at room temperature. The precipitate was filtered off and the solvent was distilled off under reduced pressure. The residue was purified by silica gel column chromatography (eluent: 1:0 to 50:1 chloroform/acetone) to give the title compound (16.80 g) as a white crystal.

$R_f$: 0.3 (20:1 chloroform/acetone).

MH$^+$: 529.

The thus obtained compound in the free form was converted into its hydrochloride using 10% hydrochloric acid/methanol (mfd. by TOKYO KASEI KOGYO).

$^1$H-NMR (CDCl$_3$: hydrochloride): 2.99 (3H, s), 3.65–3.80 (2H, m), 4.46–4.70 (4H, m), 5.03–5.18 (2H, m), 6.58 (1H, d, J=8.8), 6.92 (1H, s), 7.10 (1H, t, J=7.4), 7.29 (1H, t, J=7.4), 7.41–7.78 (10H, m), 7.91 (1H, d, J=8.8), 7.98 (1H, d, J=7.7), 10.16 (1H, s), 10.80 (1H, s), 11.20 (1H, s).

Example 2

Synthesis of 2-[N-benzyl-N-[2-(9H-carbazol-2-yloxy)]ethyl]amino-1-(4-benzyloxy-3-methylsulfonylamino)phenylethanone (Preparing Process 1)

A solution of 2-bromo-1-(4-benzyloxy-3-methylsulfonylamino)phenylethanone (10 g; prepared according to the method reported by A. A. Larsen et al., *J. Med. Chem.*, 10, p. 462 (1967)) in tetrahydrofuran (100 mL) was added dropwise to a solution of N-benzyl-N-[2-(9H-carbazol-2-yloxy)]ethylamine (15.9 g; obtained from Referential Example) in tetrahydrofuran (100 mL), followed by stirring overnight at room temperature. The precipitate was filtered off and the solvent was distilled off under reduced pressure. The residue was purified by silica gel column chromatography (eluent: 1:0 to 50:1 chloroform/acetone) to give the title compound (14.80 g) as a white crystal.

$R_f$: 0.3 (20:1 chloroform/acetone).

MH$^+$: 635.

$^1$H-NMR (CDCl$_3$): 2.92 (3H, s), 3.03 (2H, m), 3.87 (2H, s), 4.11 (2H, s), 4.16 (2H, m), 5.25 (2H, s), 6.74–8.05 (20H, m), 9.18 (1H, s), 11.05 (1H, s).

Example 3

Synthesis of (±)-2-[N-benzyl-N-[2-(9H-carbazol-2-yloxy)]ethyl]-amino-1-(3-methylsulfonylamino)phenylethanol (Preparing Process 1)

Sodium borohydride (1.44 g; mfd. by KANTO CHEMICAL) was added to a solution of 2-[N-benzyl-N-[2-(9H-carbazol-2-yloxy)]ethyl]amino-1-(3-methylsulfonylamino)phenylethanone (10 g; obtained from Example 1) in ethanol/tetrahydrofuran (1:3; 200 mL) at 0° C. The mixture was stirred at the same temperature for 3 hours. To the reaction solution were added sequentially an excess amount of ethanol and 0.1 N hydrochloric acid, followed by stirring for 30 minutes. The reaction mixture was then diluted with ethyl acetate and washed sequentially with saturated sodium bicarbonate water, water and saturated brine. After drying the organic layer on anhydrous sodium sulfate, the solvent was distilled off under reduced pressure. The residue was dried under reduced pressure to give the title compound (10.04 g) as an amorphas solid.

$R_f$: 0.33 (2:1 hexane/ethyl acetate).

MH$^+$: 531.

$^1$H-NMR (DMSO-$d_6$): 2.75 (2H, d, J=6.1), 2.91 (3H, s), 2.95–3.01 (2H, m), 3.80 (2H, brs), 4.02–4.09 (2H, m), 4.66–4.69 (2H, m), 5.47 (1H, brs), 6.73 (1H, dd J=8.4, 1.9), 6.92 (1H, d, J=2.0), 7.02–7.45 (7H, m), 7.93–8.00 (2H, m), 11.06 (1H, s).

Example 4

Synthesis of (R)-2-[N-benzyl-N-[2-(9H-carbazol-2-yloxy)]ethyl]amino-1-(3-methylsulfonylamino)phenylethanol (Preparing Process 1)

Triethylamine (0.01 mL) was added to a solution of [Rh(cod)Cl]$_2$ (87.4 mg; mfd. by Wako Pure Chemical Industries), the (2R, 4R) form (260.7 mg; mfd. by FUJI YAKUHIN) of a chiral phosphine ligand represented by the formula (16) and the hydrochloride (1 g; obtained from Example 1) in degassed methanol (3 mL) under an argon atmosphere, followed by stirring under a hydrogen atmosphere at atmospheric pressure at room temperature for 16 hours. The solvent was distilled off under reduced pressure and the residue was dissolved in ethyl acetate, which was then washed sequentially with saturated sodium bicarbonate water and saturated brine. The organic layer was dried over anhydrous sodium sulfate and then the solvent was distilled off under reduced pressure. The residue was dried under reduced pressure to give the title compound (747 mg) as an oil.

The thus obtained compound had a retention time in HPLC measurements identical to the retention time corresponding to one of the peaks of the compound obtained in Example 3.

HPLC: Retention Time (R-form: 22.0 min (S-form: 19.2 min))

Column: CHIRALPAK AD (mfd. by DAICEL CHEMICAL INDUSTRIES; 4.6 mm ID×250 mm);

Solvent: 20/80 hexane/ethanol;
Flow rate: 0.5 mL/min;
Detecting wave length: 254 nm;
Temperature: 40° C.

Example 5

Synthesis of (±)-2-[N-benzyl-N-[2-(9H-carbazol-2-yloxy)]ethyl]amino-1-(4-benzyloxy-3-methylsulfonylamino)phenylethanol (Preparing Process 1)

Sodium borohydride (1.19 g; mfd. by KANTO KAGAKU KOGYO) was added to a solution of 2-[N-benzyl-N-[2-(9H-carbazol-2-yloxy)]ethyl]amino-1-(4-benzyloxy-3-methylsulfonylamino)phenylethanone (10 g; obtained from Example 2) in ethanol/tetrahydrofuran (1:3; 200 mL) at 0° C. The mixture was stirred at the same temperature for 3 hours. To the reaction solution were added sequentially an excess amount of methanol and 0.1 N hydrochloric acid, followed by stirring for 30 minutes. The reaction mixture was then diluted with ethyl acetate and washed sequentially with saturated sodium bicarbonate water, water and saturated brine. After the organic layer was dried on anhydrous sodium sulfate, the solvent was distilled off under reduced pressure. The residue was dried under reduced pressure to give the title compound (10.03 g) as an amorphas solid.

$R_f$: 0.25 (2:1 hexane/ethyl acetate).

$MH^+$: 637.

$^1$H-NMR (CDCl$_3$): 2.8–2.9 (3H, m), 3.0–3.5 (2H, m), 3.5–3.8 (2H, m), 4.1–4.6 (5H, m), 4.9–5.0 (2H, m), 6.7–6.9 (4H, m), 7.0–7.1 (1H, m), 7.1–7.5 (11H, m), 7.5–7.7 (2H, m), 7.8–8.0 (2H, m), 8.7–8.8 (1H, m).

Example 6

Synthesis of (R)-2-[N-benzyl-N-[2-(9H-carbazol-2-yloxy)]ethyl]amino-1-(4-benzyloxy-3-methylsulfonylamino)phenylethanol (Preparing Process 1)

Triethylamine (0.01 mL) was added to a solution of [Rh(cod)Cl]$_2$ (70.4 mg; mfd. by Wako Pure Chemical Industries), the (2R, 4R) form (220 mg; mfd. by FUJI YAKUHIN) of a chiral phosphine ligand represented by the formula (16) and 2-[N-benzyl-N-[2-(9H-carbazol-2-yloxy)]ethyl]amino-1-(4-benzyloxy-3-methylsulfonylamino) phenylethanone hydrochloride (1 g; prepared from the compound 3 in the free form of Example 2 with 10% hydrochloric acid/methanol) in degassed methanol (3 mL) under an argon atmosphere, followed by stirring under a hydrogen atmosphere at atmospheric pressure at room temperature for 16 hours. The solvent was distilled off under reduced pressure and the residue was dissolved in ethyl acetate, which was then washed sequentially with saturated sodium bicarbonate water and saturated brine. The organic layer was dried over anhydrous sodium sulfate and then the solvent was distilled off under reduced pressure. The residue was dried under reduced pressure to give the title compound (876 mg) as an oil.

The thus obtained compound had a retention time in HPLC measurements identical to the retention time corresponding to one of the peaks of the compound obtained in Example 5.

HPLC: Retention Time (R-form: 35 min (S-form: 25 min))

Column: CHIRALCEL OJ-R (mfd. by DAICEL CHEMICAL INDUSTRIES; 4.6 mm ID×150 mm);

Solvent: 75/25 aqueous 0.5 M sodium perchlorate solution/acetonitrile;
Flow rate: 0.5 mL/min;
Detecting wave length: 254 nm;
Temperature: 40° C.

Example 7

Synthesis of (±)-2-[N-[2-(9H-carbazol-2-yloxy)]methyl]amino-1-(3-methylsulfonylamino)phenylethanol (Preparing Process 1)

(±)-2-[N-benzyl-N-[2-(9H-carbazol-2-yloxy)]ethyl]amino-1-(3-methylsulfonylamino)phenylethanol (10 g; obtained from Example 3) was dissolved in a mixed solvent of tetrahydrofuran (100 mL) and methanol (100 mL), to which was added a palladium hydroxide/carbon catalyst (1 g; mfd. by nacalai tesque) under a nitrogen atmosphere. The mixture was stirred overnight under a hydrogen atmosphere at atmospheric pressure at room temperature. After the catalyst was filtered off, the solvent was distilled off under reduced pressure. Crystal obtained by suction filtration was washed with a mixed solvent of tetrahydrofuran and methanol (1:1). The crystal was dissolved in methanol (150 mL) and converted into its hydrochloride by adding 0.1 N hydrochloric acid/ethanol. The precipitated crystal was obtained by suction filtration. The thus obtained crystal was dried under reduced pressure with heating at 40° C. to give the title compound in the form of hydrochloride (7.50 g) as a white crystal.

$R_f$: 0.3 (10:1 chloroform/methanol).

$MH^+$: 441.

The thus obtained compound was shown to be identical to the title compound prepared according to the known method (JP-A-9-249623) by the fact that they had the same retention time in HPLC measurements.

Example 8

Synthesis of (R)-2-N-[2-(9H-carbazol-2-yloxy)]ethyl]amino-1-(3-methylsulfonylamino)phenylethanol (Preparing Process 1)

The protecting group was removed from (R)-2-[N-benzyl-N-[2-(9H-carbazol-2-yloxy)]ethyl]amino-1-(3-methylsulfonylamino) phenylethanol (1 g; obtained from Example 4) according to the reaction conditions of Example 7 to give the title compound in the form of hydrochloride (0.75 g).

The thus obtained compound was shown to be identical to the title compound prepared according to the known method (JP-A-9-249623) by the fact that they had the same retention time in HPLC measurements.

Example 9

Synthesis of (±)-2-[N-[2-(9H-carbazol-2-yloxy)]ethyl]amino-1-(4-hydroxy-3-methylsulfonylamino)phenylethanol (Preparing Process 1)

(±)-2-[N-benzyl-N-[2-(9H-carbazol-2-yloxy)]ethyl]amino-1-(4-benzyloxy-3-methylsulfonylamino)phenylethanol (10 g; obtained from Example 5) was dissolved in a mixed solvent of tetrahydrofuran (100 mL) and methanol (100 mL), to which was added a palladium hydroxide/carbon catalyst (1 g; mfd. by nacalai tesque) under a nitrogen atmosphere. The mixture was stirred overnight under a hydrogen atmosphere at atmospheric pressure at room temperature. After the catalyst was filtered off, the solvent was distilled off under reduced pressure. The crystal obtained by suction filtration was washed with a mixed solvent of tetrahydrofuran and methanol (1:1). The crystal was then dissolved in methanol (150 mL) and converted into its hydrochloride by adding 0.1 N hydrochloric acid/ethanol (mfd. by TOKYO KASEI KOGYO). The precipitated crystal was obtained by suction filtration. The thus obtained crystal was dried under reduced pressure with heating at 40° C. to give the title compound in the form of hydrochloride (6.96 g) as a white crystal.

$R_f$: 0.3 (10:1 chloroform/methanol).

$MH^+$: 493.

The thus obtained compound was shown to be identical to the title compound prepared according to the known method (JP-A-9-249623) by the fact that they had the same retention time in HPLC measurements.

Example 10

Synthesis of (R)-2-[N-[2-(9H-carbazol-2-yloxy)] ethyl]amino-1-(4-hydroxy-3-methylsulfonylamino) phenylethanol (Preparing Process 1)

The protecting groups were removed from (R)-2-[N-benzyl-N-[2-(9H-carbazol-2-yloxy)]ethyl]amino-1-(4-benzyloxy-3-methylsulfonylamino)phenylethanol (1 g; obtained from Example 6) according to the reaction conditions of Example 9 to give the title compound in the form of hydrochloride (0.70 g).

The thus obtained compound was shown to be identical to the title compound prepared according to the known method (JP-A-9-249623) by the fact that they had the same retention time in HPLC measurements.

Example 11

Synthesis of 2-[N-benzyl-N-(2-hydroxyethyl)] amino-1-[3-(N-benzyl-N-methylsulfonylamino)] phenylethanone (Preparing Process 2)

A solution of 2-bromo-1-[3-(N-benzyl-N-methylsulfonylamino)]phenylethanone (10 g) in tetrahydrofuran (100 mL) was added dropwise to N-benzyl-2-ethanolamine (11.2 mL; mfd. by TOKYO KASEI KOGYO), followed by stirring at room temperature for 16 hours. The reaction solution was diluted with ethyl acetate, washed sequentially with water and saturated brine, and then dried over anhydrous sodium sulfate. After the solvent was distilled off under reduced pressure, the residue was recrystallized from ethanol to give the title compound (11.84 g) as a white crystal.

$R_f$: 0.2 (1:1 hexane/ethyl acetate).

$MH^+$: 454.

$^1$H-NMR (DMSO-$d_6$): 1.96–2.24 (2H, m), 2.56–2.63 (2H, m), 3.07 (3H, s), 3.45 (2H, s), 3.59 (1H, d, J=11.2), 4.08 (1H, d, J=11.2), 4.83 (2H, s), 7.16–7.44 (14H, m).

Example 12

Synthesis of 2-[N-benzyl-N-(2-bromoethyl)]amino-1-[3-(N-benzyl-N-methylsulfonylamino)] phenylethanone (Preparing Process 2)

A solution of 2-[N-benzyl-N-(2-hydroxyethyl)]amino-1-[3-(N-benzyl-N-methylsulfonylamino)]phenylethanone (10 g; obtained from Example 11) in dichloromethane (150 mL) was cooled to 0° C., to which was added a solution of phosphorus tribromide in dichloromethane (1 M; 110.5 mL; mfd. by Aldrich), followed by stirring for 15 minutes. The mixture was then stirred at 50° C. for 1 hour. The solvent was distilled off under reduced pressure and the residue was recrystallized from water/methanol to give the title compound in the form of hydrobromide (10.54 g) as a white crystal.

$R_f$: 0.62 (3:1 hexane/ethyl acetate).

$M+$: 515.

$^1$H-NMR (DMSO-$d_6$): 3.0–3.5 (7H, m), 3.5–4.5 (4H, m), 4.8–5.0 (2H, m), 7.1–8.0 (14H, m).

Example 13

Synthesis of 2-[N-benzyl-N-[2-(9H-carbazol-2-yloxy)]ethyl]amino-1-[3-(N-benzyl-N-methylsulfonylamino)]phenylethanone (Preparing Process 2)

An aqueous 2 N sodium hydroxide solution (16.8 mL) was added to a mixed solution of 2-[N-benzyl-N-(2-bromoethyl)]amino-1-[3-(N-benzyl-N-methylsulfonylamino)]phenylethanone hydrobromide (10 g; obtained from Example 12) and 2-hydroxycarbazole (4.61 g; mfd. by Aldrich) in water (50 mL) and tetrahydrofuran (150 mL) at −10° C., which was stirred at room temperature for 2 hours. The solvent was distilled off under reduced pressure and the residue was dissolved in toluene (200 mL). The organic layer was sequentially washed with an aqueous 2 N sodium hydroxide solution (four times) and saturated brine (once), and was then dried over anhydrous sodium sulfate. After the solvent was distilled off under reduced pressure, the residue was purified by silica gel column chromatography (eluent: 0:1 to 1:40 acetone/toluene) to give the title compound (9.32 g) as an oil.

$R_f$: 0.3 (1:30 acetone/toluene).

$MH^+$: 619.

The thus obtained compound in the free form was converted into its hydrochloride using 10% hydrochloric acid/methanol (mfd. by TOKYO KASEI KOGYO).

$^1$H-NMR (DMSO-$d_6$; hydrochloride): 3.12 (3H, s), 3.72 (2H, br), 4.46–4.68 (4H, m), 4.95 (2H, s), 5.12 (2H, br), 6.52 (IH, d, J=7.7), 6.95 (1H, d, J=1.9), 7.11 (1H, t, J=7.7), 7.16–7.34 (6H, m), 7.40–7.50 (4H, m), 7.54 (1H, t, J=8.2), 7.66–7.78 (3H, m), 7.83 (1H, d, J=7.7), 7.85 (1H, d, J=8.5), 7.95–8.02 (2H, m), 10.79 (1H, br), 11.23 (1H, br).

Example 14

Synthesis of 2-[N-benzyl-N-[2-(9H-carbazol-2-yloxy)]ethyl]amino-1-[3-(N-benzyl-N-methylsulfonylamino)]phenylethanone (Preparing Process 2)

1,1'-(Azodicarbonyl)dipiperidine (8.36 g; mfd. by TOKYO KASEI KOGYO) was added to a solution of 2-[N-benzyl-N-(2-hydroxyethyl)]amino-1-[3-(N-benzyl-N-methylsulfonylamino)]phenylethanone (10 g; obtained from Example 11), 2-hydroxycarbazole (6.07 g) and tri-n-butylphosphine (6.71 g; mfd. by TOKYO KASEI KOGYO) in tetrahydrofuran (200 mL), which was stirred at room temperature for 12 hours. The precipitated crystal was filtered off and the solvent was distilled off under reduced pressure. The residue was purified by silica gel column chromatography (eluent: 0:1 to 1:40 acetone/toluene) to give the title compound (10.24 g) as an oil.

The thus obtained compound was shown to be identical to the title compound obtained in Example 13 by the fact that they had the same retention time in HPLC measurements.

Example 15

Synthesis of (±)-2-[N-[2-(9H-carbazol-2-yloxy)]ethyl]amino-1-(3-methylsulfonylamino)phenylethanol (Preparing Process 2)

The compound (5 g; obtained from Example 13) was subjected to the synthesizing procedure according to Examples 3 and 7 to give the title compound in the form of hydrochloride (3.77 g) as a white crystal.

The thus obtained compound was shown to be identical to the title compound prepared according to the known method (JP-A-9-249623) by the fact that they had the same retention time in HPLC measurements.

Example 16

Synthesis of (±)-2-[N-benzyl-N-(2-bromoethyl)]amino-1-[3-(N-benzyl-N-methylsulfonylamino)]phenylethanol (Preparing Process 3)

Sodium borohydride (1.27 g; mfd. by KANTO CHEMICAL) was added to a solution of 2-[N-benzyl-N-(2-bromoethyl)]amino-1-[3-(N-benzyl-N-methylsulfonylamino)]phenylethanone hydrobromide (10 g; obtained from Example 12) in methanol (300 mL) at 0° C., which was stirred at the same temperature for 3 hours. To the reaction solution were added sequentially water (50 mL) and 0.1 N hydrochloric acid (50 mL), followed by stirring for 30 minutes. After the solvent was distilled off under reduced pressure, the precipitated crystal was recrystallized from water/methanol to give the title compound in the form of hydrochloride (8.82 g) as a white crystal.

$R_f$: 0.4 (2:1 hexane/ethyl acetate).
MH$^+$: 518

Example 17

Synthesis of (R)-2-[N-benzyl-N-(2-bromoethyl)]amino-1-[3-(N-benzyl-N-methylsulfonylamino)]phenylethanol (Preparing Process 3)

The compound in the form of hydrobromide (1 g; obtained from Example 12) was treated according to Example 4 to give the title compound in the form of hydrochloride (864 mg).

$^1$H-NMR (CDCl$_3$): 2.39–2.48 (1H, m), 2.66–2.71 (1H, m), 2.85–2.94 (1H, m), 2.92 (3H, s), 2.99–3.08 (1H, m), 3.40 (2H, t, d=6.4), 3.58 (1H, d, J=13.4), 3.84 (1H, s), 3.88 (1H, d, J=13.4), 4.59 (1H, dd, J=3.3, 10.1), 4.82 (2H, s), 7.12–7.39 (14H, m).

Example 18

Synthesis of (±)-2-[N-benzyl-N-[2-(9H-carbazol-2-yloxy)]ethyl]amino-1-[3-(N-benzyl-N-methylsulfonylamino)]phenylethanol (Preparing Process 3)

An aqueous 2 N sodium hydroxide solution (45.1 mL) was added to a mixed solution of (±)-2-[N-benzyl-N-(2-bromoethyl)]amino-1-[3-(N-benzyl-N-methylsulfonylamino)]phenylethanol hydrochloride (10 g; obtained from Example 16) and 2-hydroxycarbazole (4.96 g) in water (50 mL) and tetrahydrofuran (150 mL) at −10° C., which was stirred at room temperature for 2 hours. The solvent was distilled off under reduced pressure and the residue was dissolved in toluene (200 mL). The organic layer was washed sequentially with an aqueous 2 N sodium hydroxide solution (four times) and saturated brine (once), and then dried over anhydrous sodium sulfate. After the solvent was distilled off under reduced pressure, the residue was purified by silica gel column chromatography (eluent: 0:1 to 1:20 acetone/toluene) to give the title compound (6.22 g) as an oil.

$R_f$: 0.3 (1:20 acetone/toluene)

Example 19

Synthesis of (±)-2-[N-[2-(9H-carbazol-2-yloxy)]ethyl]amino-1-(3-methylsulfonylamino)phenylethanol (Preparing Process 3)

The protecting groups were removed from (±)-2-[N-benzyl-N-[2-(9H-carbazol-2-yloxy)]ethyl]amino-1-[3-(N-benzyl-N-methylsulfonylamino)]phenylethanol (5 g; obtained from Example 18) according to the reaction conditions of Example 7 to give the title compound in the form of hydrochloride (3.75 g).

The thus obtained compound was shown to be identical to the title compound prepared according to the known method (JP-A-9-249623) by the fact that they had the same retention time in HPLC measurements.

Example 20

Synthesis of (±)-2-[N-benzyl-N-(2-hydroxyethyl)]amino-1-[3-(N-benzyl-N-methylsulfonylamino)]phenylethanol (Preparing Process 4)

Sodium borohydride (1.67 g; mfd. by KANTO CHEMICAL) was added to a solution of 2-[N-benzyl-N-(2-hydroxyethyl)]amino-1-[3-(N-benzyl-N-methylsulfonylamino)]phenylethanone (10 g; obtained from Example 11) in ethanol/tetrahydrofuran (1:3; 232 mL) at 0° C., which was stirred at the same temperature for 3 hours. To the reaction solution were added sequentially an excess amount of methanol and 0.1 N hydrochloric acid, followed by stirring for 30 minutes. The reaction solution was diluted with ethyl acetate, washed sequentially with saturated sodium bicarbonate water, water and saturated brine, and then dried over anhydrous sodium sulfate. After the solvent was distilled off under reduced pressure, the crystal obtained was dried under reduced pressure to give the title compound (10.06 g) as a white crystal.

$R_f$: 0.2 (1:1 hexane/ethyl acetate).
MH$^+$: 456
$^1$H-NMR (CDCl$_3$): 2.55 (1H, dd, J=13.5, 9.3), 2.61–2.71 (2H, m), 2.76–2.86 (1H, m), 2.91 (3H, s), 3.54–3.72 (3H, m), 3.83 (1H, d, J=13.5), 4.61 (1H, dd, J=9.3, 3.9), 4.82 (2H, s), 7.10–7.37 (14H, m).

Example 21

Synthesis of (±)-2-[N-benzyl-N-[2-(9H-carbazol-2-yloxy)]ethyl]amino-1-[3-(N-benzyl-N-methylsulfonylamino)]phenylethanol (Preparing Process 4)

1,1'-(Azodicarbonyl)dipiperidine (5.55 g) was added to a solution of (±)-2-[N-benzyl-N-(2-hydroxyethyl)]amino-1-[3-(N-benzyl-N-methylsulfonylamino)]phenylethanol (10 g; obtained from Example 20), 2-hydroxycarbazole (4.03 g) and tri-n-butylphosphine (4.45 g) in tetrahydrofuran (200 mL), which was stirred at room temperature for 12 hours. The precipitated crystal was filtered off and the solvent was distilled off under reduced pressure. The residue was purified by silica gel column chromatography (eluent: 0:1 to 1:20 acetone/toluene) to give the title compound (9.54 g) as an oil.

The thus obtained compound was shown to be identical to the compound obtained from Example 18 by the fact that they had the same retention time in HPLC measurements.

Example 22

Synthesis of (±)-2-[N-benzyl-N-(2-bromoethyl)] amino-1-[3-(N-benzyl-N-methylsulfonylamino)] phenylethanol (Preparing Process 4)

A solution of (±)-2-[N-benzyl-N-(2-hydroxyethyl)] amino-1-[3-(N-benzyl-N-methylsulfonylamino)] phenylethanol (10 g; obtained from Example 20) in dichloromethane (150 mL) was cooled to 0° C., to which was added a solution of phosphorus tribromide in dichloromethane (1 M; 66.0 mL; mfd. by Aldrich), followed by stirring for 15 minutes. The mixture was then stirred at 50° C. for 1 hour. The solvent was distilled off under reduced pressure and the residue was recrystallized from water/ methanol to give the title compound in the form of hydrobromide (9.87 g) as a white crystal.

Example 23

Synthesis of (±)-2-[N-benzyl-N-[2-(9H-carbazol-2-yloxy)]ethyl]amino-1-[3-(N-benzyl-N-methylsulfonylamino)]phenylethanol (Preparing Process 4)

The compound in the form of hydrobromide (5 g; obtained from Example 22) was treated according to Example 18 to give the title compound (3.10 g).

The thus obtained compound was shown to be identical to the compound obtained in Example 18 by the fact that they had the same retention time in HPLC measurements.

Example 24

Synthesis of 2-[N-benzyl-N-(2-bromoethyl)]amino-1-[3-(N-benzyl-N-methylsulfonylamino)] phenylethanone Hydrochloride (Preparing Process 5)

An aqueous 2 N sodium hydroxide solution (32.7 mL) was slowly added dropwise to a mixed solution of 2-bromo-1-[3-(N-benzyl-N-methylsulfonylamino)]phenylethanone (5 g) and 2-bromoethylamine hydrobromide (13.40 g; mfd. by TOKYO KASEI KOGYO) in tetrahydrofuran (90 mL) and water (10 mL) at room temperature, followed by stirring at the same temperature for 5 hours. The reaction solution was then adjusted to pH 1 with 3 N hydrochloric acid. The precipitated crystal was washed with water and dried under reduced pressure to give the title compound (3.02 g) as a white crystal.

$MH^+$: 426.

Example 25

Synthesis of (R)-2-[N-(2-bromoethyl)]ethylamino-1-[3-(N-benzyl-N-methylsulfonylamino)] phenylethanol Hydrochloride (Preparing Process 5)

The compound (1.5 g; obtained from Example 24) was treated according to Example 4 to give the title compound in the form of hydrochloride (1.37 g).

$MH^+$: 428.

Example 26

Synthesis of (R)-2-[N-(tert-butoxycarbonyl)-N-[2-(9H-carbazol-2-yloxy)]ethyl]amino-1-[3-(N-benzyl-N-methylsulfonylamino)]phenyethanol (Preparing Process 5)

Triethylamine (3.69 mL) was slowly added dropwise to a mixed solution of (R)-2-[N-[2-(9H-carbazol-2-yloxy)]ethyl] amino-1-[3-(N-benzyl-N-methylsulfonylamino)] phenylethanol hydrochloride (1 g; obtained from Example 25) and di-tert-butyl dicarbonate (5.78 g; mfd. by Wako Pure Chemical Industries) in water (50 mL) and methanol (150 mL) at 0° C. The reaction solution was stirred overnight at room temperature and then the solvent was distilled off under reduced pressure. The residue was dissolved in ethyl acetate, washed sequentially with water and saturated sodium bicarbonate water, and then dried over anhydrous sodium sulfate. The solvent was distilled off under reduced pressure and the residue was recrystallized from ethanol to give the title compound (1.11 g) as a white crystal.

$R_f$: 0.5 (1:1 hexane/ethyl acetate).
$MH^+$: 631.

Example 27

Synthesis of (R)-2-[N-[2-(9H-carbazol-2-yloxy)] ethyl]amino-1-(3-methylsulfonylamino) phenylethanol (Preparing Process 5)

A 10% hydrochloric acid/methanol solution was added to a solution of (R)-2-[N-(tert-butoxycarbonyl)-N-[2-(9H-carbazol-2-yloxy)]ethyl]amino-1-[3-(N-benzyl-N-methylsulfonylamino)]phenylethanol (1 g; obtained from Example 26) in methanol (200 mL) at 0° C., which was stirred at room temperature for 6 hours. The solvent was distilled off under reduced pressure. A crystal obtained by suction filtration was washed with methanol/diethylether (1:1) and then dried under reduced pressure with heating (40° C.) to give the corresponding BOC (tert-butoxycarbonyl)-removed compound (872 mg; in the form of hydrochloride) as a white crystal. The said hydrochloride (500 mg) was dissolved in a mixed solvent of tetrahydrofuran (7.5 mL) and water (1.5 mL), to which was added a palladium hydroxide/carbon catalyst (50 mg) under a nitrogen atmosphere. The mixture was stirred overnight under a hydrogen atmosphere at atmospheric pressure at room temperature. After the catalyst was filtered off, the solvent was distilled off under reduced pressure. A crystal obtained by suction filtration was washed with methanol and then dried under reduced pressure with heating (40° C.) to give the title compound in the form of hydrochloride (391 mg) as a white crystal.

$R_f$: 0.5 (10:1 chloroform/methanol).
$MH^+$: 441.

The thus obtained compound was shown to be identical to the title compound prepared according to the known method (JP-A-9-249623) by the fact that they had the same retention time in HPLC measurements.

Example 28

Synthesis of 2-[N-benzyl-N-[2-(9H-carbazol-2-yloxy)]ethyl]amino-1-[3-(N-benzyl-N-methylsulfonylamino)]phenylethanone Hydrochloride (Preparing Process (1)

Step A. Synthesis of 1-[3-(N-benzyl-N-methylsulfonylamino)]phenylethanone

1-[3-(N-methylsulfonylamino)]phenylethanone (90.68 g; prepared according to the method reported by A. A. Larsen et al., *J. Med. Chem.,* 9, pp. 88–97 (1966)) was dissolved in acetone (639.6 mL) at 23° C., to which was added anhydrous potassium carbonate (66.0 g). Benzyl bromide (56.6 mL; mfd. by Wako Pure Chemical Industries) was added all at once to the mixture with stirring. Subsequently, sodium iodide (13.01 g; mfd. by Wako Pure Chemical Industries) was added to the mixture, which was heated to reflux with stirring vigorously. After 2 hours, anhydrous potassium carbonate (29.4 g) and sodium iodide (32 g) were added to the mixture, which was further stirred. After further 1 hour, anhydrous potassium carbonate (29.4 g) and sodium iodide (32 g) were added to the mixture, which was stirred vigorously at the same temperature for 13.5 hours. The mixture was allowed to cool to 43° C. and purified water (1090 mL) was then added all at once. The mixture was stirred vigorously and then extracted with ethyl acetate (495 mL). The organic layer was separated, washed with saturated brine (495 mL) and dried over anhydrous magnesium sulfate (90 g) for 0.5 hour. After the drying agent was filtered off, the solvent was distilled off under reduced pressure. The thus obtained crude product (139.42 g) was suspended in ethyl acetate (343 mL), to which was added n-hexane (445 mL) with heating under reflux. Further, ethyl acetate (20 mL) was added to the mixture with heating under reflux to completely dissolve the crude product, which was then recrystallized with stirring under ice cooling to give the title compound (71.71 g).

$R_f$: 0.44 (1:1 ethyl acetate/n-hexane).

$^1$H-NMR (CDCl$_3$): 2.55 (3H, s), 2.97 (3H, s), 4.88 (2H, s), 7.20–7.30 (5H, m), 7.41 (1H, m), 7.46 (1H, dt, J=8.2, 1.9), 7.81–7.86 (2H, m).

Step B. Synthesis of 2-bromo-1-[3-(N-benzyl-N-methylsulfonyl-amino)]phenylethanone The compound (71.21 g; synthesized in Step A) was dissolved in methanol (3.94 L), to which was added all at once tetra-n-butylammonium tribromide (127g; mfd. by Aldrich). After stirring at room temperature for 13 hours, a mixed solution of 47% hydrobromic acid (985 mL) and purified water (985 mL) was added all at once to the mixture, which was further stirred for 1 hour while maintaining the internal temperature at 35 to 40° C. Purified water (985 mL) was added to the mixture, which was slowly cooled down to a internal temperature of 30° C. with stirring vigorously over 3 hours and was then further cooled down to 5° C. followed by further stirring for 2 hours. The precipitated crystal obtained by filtration was washed twice with a mixed liquid (2.5 L) of methanol and water. The wet crystal was dried under reduced pressure at 50° C. for 24 hours to give the title compound (73.80 g).

$R_f$: 0.46 (1:1 ethyl acetate/n-hexane).

$^1$H-NMR (CDCl$_3$): 2.98 (3H, s), 4.36 (2H, s), 4.89 (2H, s), 7.20–7.30 (5H, m), 7.44 (1H, t, J=8.0), 7.51 (1H, dt, J=8.0, 1.7), 7.84–7.89 (2H, m).

Step C. Synthesis of 2-[N-benzyl-N-[2-(9H-carbazol-2-yloxy)]ethyl]amino-1-[3-(N-benzyl-N-methylsulfonylamino)]phenylethanone Monohydrochloride The compound (40.26 g; obtained from Reference Example) was added to a solution of the compound (22.94 g; obtained from Step B) in tetrahydrofuran (1.57 L), which was stirred overnight. After the precipitate was filtered off, concentrated hydrochloric acid (7.2 mL) was added to the mixture. The precipitate was filtered and the filtrate was then concentrated and kneading washed with 2-propanol (720 mL) to give a crude product. This was further kneading washed with methanol (275 mL), filtered and dried under reduced pressure at 40° C., and then further kneading washed with methanol (180 mL), filtered and dried under reduced pressure at 40° C. to give the title compound (20.54 g).

$R_f$: 0.43 (1:1 ethyl acetate/n-hexane).

$^1$H-NMR (DMSO-d$_6$; hydrochloride): 3.12 (3H, s), 3.72 (2H, br), 4.46–4.68 (4H, m), 4.95 (2H, s), 5.12 (2H, br), 6.52 (1H, d, J=7.7), 6.95 (1H, d, J=1.9), 7.11 (1H, t, J=7.7), 7.16–7.34 (6H, m), 7.40–7.50 (4H, m), 7.54 (1H, t, J=8.2), 7.66–7.78 (3H, m), 7.83 (1H, d, J=7.7), 7.85 (1H, d, J=8.5), 7.95–8.02 (2H, m), 10.79 (1H, br), 11.23 (1H, br).

Example 29

Synthesis of (R)-2-[N-benzyl-N-[2-(9H-carbazol-2-yloxy)]ethyl]amino-1-[3-(N-benzyl-N-methylsulfonylamino)]phenylethanol (Preparing Process 1)

The compound obtained from Example 28 was treated according to Example 4 to give the title compound.

$R_f$: 0.27 (1:1 n-hexane/ethyl acetate).

$^1$H-NMR (DMSO-d$_6$): 2.65–2.72 (2H, m), 2.91 (2H, m), 3.05 (3H, s), 3.76 (2H, br, s), 3.95–4.03 (2H, m), 4.65–4.73 (1H, m), 4.82 (2H, s), 5.15 (1H, d, J=3.6), 6.72 (1H, dd, J=8.5, 2.2), 6.90 (1H, d, J=2.2), 7.08–7.37 (16H, m), 7.42 (1H, d, J=8.0), 7.95 (1H, d, J=8.5), 7.99 (1H, d, J=7.7), 11.08 (1H, s).

HPLC: Retention Time (R-form: 25.0 min (S-form: 18.2 min))

Chiral column: CHIRALCEL OJ-R(mfd. by DAICEL CHEMICAL INDUSTRIES; 4.6 mm ID×150 mm);

Solvent: 30/70 0.5 M NaClO$_4$ aq./acetonitrile;

Flow rate: 0.5 mL/min;

Detecting wave length: 233 nm;

Temperature: 40° C.

Example 30

Synthesis of (R)-2-[N-[2-(9H-carbazol-2-yloxy)] ethyl]amino-1-(3-methylsulfonylamino) phenylethanol (Preparing Process 1)

The protecting group was removed from (R)-2-[N-benzyl-N-[2-(9H-carbazol-2-yloxy)]ethyl]amino-1-(3-methylsulfonylamino)phenylethanol (1 g; obtained from Example 29) according to the reaction conditions of Example 7 to give the title compound in the form of hydrochloride (0.7 g).

The thus obtained compound was shown to be identical to the title compound prepared according to the known method (JP-A-9-249623) by the fact that they had the same retention time in HPLC measurements.

Example 31

Synthesis of 2-[N-benzyl-N-[2-(9H-carbazol-2-yloxy)]ethyl]amino-1-(4-chloro-3-methylsulfonylamino)phenylethanone (Preparing Process 1)

A solution of N-benzyl-N-[2-(9H-carbazol-2-yloxy)] ethylamine (51.1 g; obtained from Reference Example) in tetrahydrofuran (1.53 L) was added dropwise to a solution of 2-bromo-1-(4-chloro-3-methylsulfonylamino)

phenylethanone (25 g; prepared according to the method reported by A. A. Larsen et al., *J. Med. Chem.*, 10, p. 462 (1967)) in tetrahydrofuran (382 mL), which was stirred overnight at room temperature. The precipitate was filtered off and the solvent was distilled off under reduced pressure. The residue was purified by silica gel column chromatography (eluent: 5:1 to 1:1 hexane/ethyl acetate). After the eluate was concentrated, the crystal was washed with a mixed solvent of hexane and ethyl acetate (1:1) to give the title compound (17.46 g) as a pale cream crystal.

$R_f$: 0.42 (1:1 hexane/ethyl acetate).

$MH^+$: 547

$^1$H-NMR (CDCl$_3$): 3.00–3.08 (5H, m), 3.88 (2H, s), 4.15 (2H, t, J=5.5), 4.18 (2H, s), 6.65 (1H, dd, J=2.2, 8.5), 6.90 (1H, d, J=2.2), 7.10 (1H, t, J=7.4), 7.25–7.42 (8H, m), 7.63 (1H, d, J=8.5), 7.83 (1H, dd, J=2.2, 8.5), 7.91 (1H, d, J=8.5), 7.97 (1H, d, J=8.5), 7.99 (1H, d, J=2.2).

Example 32

Synthesis of (R)-2-[N-benzyl-N-[2-(9H-carbazol-2-yloxy)]ethyl]amino-1-(4-chloro-3-methylsulfonylamino)phenylethanol (Preparing Process 1)

The compound obtained from Example 31 was treated according to Example 4 to give the title compound.

$R_f$: 0.40 (1:1 ethyl acetate/n-hexane).

$MH^+$: 486

$^1$H-NMR (CDCl$_3$): 2.68 (1H, dd, J=12.8, 10.2), 2.84 (1H, dd, J=13.0, 3.4), 3.01 (1H, dt, J=5.0, 14.2), 3.14 (1H, dt, J=5.9, 14.2), 3.72 (1H, d, J=13.5), 3.96 (2H, m), 4.11 (2H, m), 4.61 (1H, dd, J=3.4, 10.0), 6.60 (1H, dd, J=2.0, 8.2), 6.76 (1H, d, J=2.0), 6.86 (2H, m), 7.14–7.37 (9H, m), 7.90–7.98 (3H, m).

HPLC: Retention Time (R-form: 22.0 min (S-form: 27.6 min))

Chiral column: CHIRALPAK AD(mfd. by DAICEL CHEMICAL INDUSTRIES; 4.6 mm ID×250 mm);

Solvent: 20/80 n-hexane/ethanol;

Flow rate: 0.5 mL/min;

Detecting wave length: 254 nm;

Temperature: 40° C.

Example 33

Synthesis of (R)-2-[N-[2-(9H-carbazol-2-yloxy)]ethyl]amino-1-(4-chloro-3-methylsulfonylamino)phenylethanol (Preparing Process 1)

The protecting group was removed from (R)-2-[N-benzyl-N-[2-(9H-carbazol-2-yloxy)]ethyl]amino-1-(4-chloro-3-methylsulfonylamino)phenylethanol (1 g; obtained from Example 32) according to the reaction conditions of Example 7 to give the title compound in the form of hydrochloride (0.65 g).

The thus obtained compound was shown to be identical to the title compound prepared according to the known method (JP-A-9-249623) by the fact that they had the same retention time in HPLC measurements.

Example 34

Synthesis of 2-[N-benzyl-N-[2-(9H-carbazol-2-yloxy)]ethyl]amino-1-[4-chloro-3-(N-benzyl-N-methylsulfonylamino)]phenylethanone Monohydrochloride (Preparing Process 1)

Step A. Synthesis of 1-[4-chloro-3-(N-benzyl-N-methylsulfonyl-amino)]phenylethanone 1-[4-Chloro-3-(N-methylsulfonylamino)]phenylethanone (90.68 g; synthesized by the method disclosed in WO 97/25311) was dissolved in DMF (50 mL) at 23° C., to which was added anhydrous potassium carbonate (31.7 g). Benzyl bromide (21.6 g; mfd. by Wako Pure Chemical Industries) was added all at once to the mixture with stirring, which was then stirred vigorously at the same temperature for 2.5 days. After purified water (200 mL) was added all at once and stirred vigorously, the mixture was extracted with ethyl acetate (200 mL) and n-heptane (50 mL). The organic layer was separated, washed with purified water (100 mL; twice) and saturated brine (200 mL) and dried over anhydrous sodium sulfate. After the drying agent was filtered off, the solvent was distilled off under reduced pressure. The thus obtained crude product was purified by column chromatography on silica gel (1.5 kg) and the title compound (27.63 g) was obtained as a pale yellow oil from the fraction eluted with ethyl acetate/n-hexane (1:4 to 3:7).

$R_f$: 0.43 (1:1 ethyl acetate/n-hexane).

$^1$H-NMR (CDCl$_3$): 2.40 (3H, s), 3.08 (3H, s), 4.58 (1H, br), 5.09 (1H, br), 7.22–7.32 (5H, m), 7.53 (1H, d, J=8.2), 7.56 (1H, d, J=2.2), 7.82 (1H, dd, J=8.2, 2.2).

Step B. Synthesis of 2-bromo-1-[4-chloro-3-(N-benzyl-N-methylsulfonylamino)]phenylethanone The compound (58.31 g; obtained from Step A) was dissolved in 1,4-dioxane (583.1 mL), to which tetra-n-butylammonium tribromide (91.55 g; mfd. by TOKYO KASEI KOGYO) was added all at once. The reaction solution was stirred at room temperature for 15 hours, and then concentrated under reduced pressure. The thus obtained residue was purified twice by column chromatography on silica gel (1.0 kg) and the title compound (54.26 g) was obtained from the fraction eluted with ethyl acetate/n-hexane (1:5 to 1:2).

$R_f$: 0.44 (1:1 ethyl acetate/n-hexane).

$^1$H-NMR (CDCl$_3$): 3.09 (3H, s), 4.21 (2H, br-s), 4.60 (1H, br), 5.11 (1H, br), 7.22–7.32 (5H, m), 7.57 (1H, d, J=8.5), 7.61 (1H, d, J=2.2), 7.87 (1H, dd, J=8.5, 2.2).

Step C. Synthesis of 2-[N-benzyl-N-[2-(9H-carbazol-2-yloxy)]ethyl]amino-1-[4-chloro-3-(N-benzyl-N-methylsulfonylamino)]phenylethanone Monohydrochloride The compound (34.17 g; obtained from Step B) was reacted with N-benzyl-N-[2-(9H-carbazol-2-yloxy)]ethylamine (54.48 g; obtained from Reference Example) according to the synthesizing method of Example 31. The reaction product was purified by silica gel column chromatography (eluent: 1:4 to 3:7 ethyl acetate/n-hexane) and then solidified as its hydrochloride, which was kneading washed with 2-propanol and then dried under reduced pressure to give the title compound (17.64 g).

$R_f$: 0.51 (1:1 ethyl acetate/n-hexane).

$^1$H-NMR (DMSO-d$_6$; hydrochloride): 3.27 (3H, s), 3.72 (2H, m), 4.49–4.72 (4H, m), 4.93 (2H, m), 5.16 (2H, br), 6.55 (1H, d, J=8.0), 6.97 (1H, d, J=1.9), 7.11 (1H, t, J=7.7), 7.18–7.35 (6H, m), 7.39–7.58 (4H, m), 7.65–7.78 (3H, m), 7.83 (1H, t, J=8.5), 7.89 (1H, d, J=8.5), 7.98 (1H, d, J=7.7), 8.08 (1H, s), 11.01 (1H, br), 11.27 (1H, s).

Example 35

Synthesis of (R)-2-[N-benzyl-N-[2-(9H-carbazol-2-yloxy)]ethyl]amino-1-[4-chloro-3-(N-benzyl-N-methylsulfonylamino)]phenylethanol (Preparing Process 1)

The compound obtained from Example 34 was treated according to Example 4 to give the title compound.

R$_f$: 0.64 (1:1 ethyl acetate/n-hexane).

$^1$H-NMR (CDCl$_3$): 2.91 (2H, m), 3.16 (3H, s), 3.75 (2H, m), 4.02 (2H, m), 4.61–4.82 (4H, m), 5.23 (1H, m), 6.72 (1H, dd, J=8.5, 2.2), 6.92 (1H, d, J=2.2), 7.07–7.44 (16H, m), 7.93–8.01 (2H, m), 11.07 (1H, s).

HPLC: Retention Time (R-form: 27.0 min (S-form: 20.9 min))

Chiral column: CHIRALCEL OJ-R(mfd. by DAICEL CHEMICAL INDUSTRIES; 4.6 mm ID×150 mm);

Solvent: 30/70 0.5 M NaClO$_4$ aq./acetonitrile;

Flow rate: 0.5 mL/min;

Detecting wave length: 233 nm;

Temperature: 40° C.

Example 36

Synthesis of (R)-2-[N-[2-(6-hydroxy-9H-carbazol-2-yloxy)]ethyl]amino-1-(3-methylsulfonylamino) phenylethanol Hydrochloride (Preparing Process 4)

Step A. Synthesis of 2-methoxy-6-hydroxycarbazole

2-Nitro-4-methoxyaniline (16.8 g) was added to water (30 mL) and concentrated hydrochloric acid (160 mL). The mixture was stirred at room temperature for 20 minutes and further at 70° C. for 75 minutes. An aqueous solution (30 mL) containing sodium nitrite (11.5 g) was added dropwise to the reaction solution while the reaction solution was maintained at a temperature of 5° C. or less by ice cooling. After the adding was completed, the reaction solution was stirred for 1 hour while maintained at 10° C. The reaction solution was filtered and the residue was washed with water (50 mL). The filtrate was cooled with ice, to which a mixed aqueous solution (120 mL) of sodium hydrogencarbonate (123 g) and 1,4-benzoquinone (12.3 g) was added dropwise over 1 hour. After the adding was completed, the reaction solution was stirred for 4 hours with ice cooling and then filtered. The thus obtained crystal was washed with water, dried, and then dissolved in methanol (200 mL) and acetic acid (20 mL). 10% Palladium/carbon (1.0 g) was added to the mixture, which was stirred under a hydrogen atmosphere at room temperature for 3 hours. The reaction solution was filtered and the residue was washed with methanol (30 mL). Concentrated aqueous ammonia (50 mL) was added dropwise to the filtrate with ice cooling over 5 minutes. After the adding was completed, the reaction solution was allowed to warm to room temperature and stirred for 12 hours. The reaction solution was filtered and the crystal was washed with water and then dried under reduced pressure. The thus obtained crude product was purified by silica gel column chromatography (eluent: 3:1 to 0:1 hexane/ethyl acetate) to give the title compound (2.71 g).

R$_f$: 0.38 (1:1 ethyl acetate/n-hexane).

$^1$H-NMR (DMSO-d$_6$): 3.82 (3H, s), 6.68 (1H, dd, J=2.2, 8.5), 6.77 (1H, dd, J=2.2, 8.5), 6.88 (1H, d, J=2.2), 7.20 (1H, d, J=8.5), 7.30 (1H, d, J=2.2), 7.83 (1H, d, J=8.5), 8.82 (1H, br), 10.73 (1H, br).

Step B. Synthesis of 2-methoxy-6-benzyloxycarbazole

The compound (3.90 g; synthesized in Step A) was dissolved in acetone (90 mL) and DMF (6 mL), to which were added potassium carbonate (10.1 g) and benzyl bromide (3.12 g). The mixture was stirred at room temperature for 25 hours. Benzyl bromide (1.56 g) was added to the mixture which was further stirred at room temperature for 24 hours. Water (500 mL) was added to the reaction solution. The precipitated crystal obtained by filtration was washed with water and then dried in vacuo. The thus obtained crude product was added to ethyl acetate (40 mL), which was then stirred for 10 minutes. The crystal obtained by filtration was dried under reduced pressure to give the title compound (3.28 g).

R$_f$: 0.66 (1:1 ethyl acetate/n-hexane).

$^1$H-NMR (DMSO-d$_6$): 3.83 (3H, s), 5.16 (2H, s), 6.73 (1H, dd, J=2.2, 8.5), 6.92 (1H, d, J=2.2), 6.99 (1H, dd, J=2.5, 8.5), 7.30–7.43 (4H, m), 7.50–7.52 (2H, m), 7.67 (1H, d, J=2.2), 7.92 (1H, d, J=8.5), 10.90 (1H, br).

Step C. Synthesis of 2-hydroxy-6-benzyloxycarbazole

The compound (5.93 g; obtained from Step B) was dissolved in DMSO (110 mL), to which sodium cyanide (5.75 g) was added. The mixture was stirred at 170° C. for 7 hours. Water (150 mL) was added to the reaction solution, which was then extracted with ethyl acetate. The organic layer was washed with water and then dried, followed by distilling off the solvent under reduced pressure. The residue was purified by silica gel column chromatography (eluent: 1:1 hexane/ethyl acetate) to give the 1:1 mixture (1.24 g) of the title compound and 2-methoxy-6-hydroxycarbazole.

R$_f$: 0.69 (1:1 ethyl acetate/n-hexane).

The following is a spectral data of 2-hydroxy-6-benzyloxycarbazole.

$^1$H-NMR (DMSO-d$_6$): 5.15 (2H, s), 6.59 (1H, dd, J=2.2, 8.2), 6.76 (1H, d, J=2.5), 6.95 (1H, dd, J=2.5, 8.5), 7.26 (1H, d, J=8.5), 7.32–7.43 (3H, m), 7.49–7.52 (2H, m), 7.60 (1H, d, J=2.5), 7.80 (1H, d, J=8.2), 9.35 (1H, br), 10.72 (1H, br).

Step D. Synthesis of (R)-2-[N-benzyl-N-[2-(6-benzyloxy-9H-carbazol-2-yloxy)]ethyl]amino-1-[3-(N-benzyl-N-methylsulfonylamino)]phenylethanol The compound obtained from Example 11 was reduced according to Example 4 to give (R)-2-[N-benzyl-N-(2-hydroxyethyl)]amino-1-[3-(N-benzyl-N-methylsulfonylamino)]phenylethanol.

N-bromosuccinimide (2.04 g; mfd. by TOKYO KASEI KOGYO) was added to a solution of the above obtained compound (5.3 g) and triphenylphosphine (2.98 g; mfd. by Wako Pure Chemical Industries) in dehydrated dichloromethane (100 mL) at −15° C., which was then stirred for 10 minutes (bromine-form: Rf=0.91 (1:9 methanol/chloroform)). The reaction was completed, the reaction product was purified by silica gel column (eluent: 4:1 to 2:1 n-hexane/ethyl acetate) and then concentrated.

The 1:1 mixture of 2-hydroxy-6-benzyloxycarbazole and 2-methoxy-6-hydroxycarbazole (1.0 g; obtained from Step C) was dissolved in tetrahydrofuran (25 mL), to which an aqueous 2 N sodium hydroxide solution (3.45 mL) was added at room temperature.

To this added was all at once a previously prepared solution of the said bromine-form in tetrahydrofuran (25 mL), followed by stirring at room temperature for 17 hours. The solvent was distilled off under reduced pressure. The residue was dissolved in ethyl acetate, washed sequentially with an aqueous 2 N sodium hydroxide solution and water, and then dried. After the solvent was distilled off, the residue was purified by silica gel column chromatography (eluent: 3:1 to 1:1 hexane/ethyl acetate) to give the 1:1 mixture (2.71 g) of the title compound and a by-product, (R)-2-[N-benzyl-N-[2-(2-methoxy-9H-carbazol-6-yloxy)]ethyl]amino-1-[3-(N-benzyl-N-methylsulfonylamino)]phenylethanol.

Step E. Synthesis of (R)-2-[N-[2-(6-hydroxy-9H-carbazol-2-yloxy)]ethyl]amino-1-(3-methylsulfonylamino)phenylethanol Hydrochloride The mixture (2.4 g) of (R)-2-[N-benzyl-N- [2-(6-benzyloxy-9H-carbazol-2yloxy)]ethyl]amino-1-[3-(N-benzyl-N-methylsulfonylamino)]phenylethanol and the said by-product was dissolved in a mixed solvent of tetrahydrofuran (35 mL) and methanol (35 mL), to which acetic acid (2.4 mL) was added. After 20% palladium hydroxide/carbon (1.2 g) was added to the mixture under an argon atmosphere and the atmosphere was replaced with hydrogen, the resulting mixture was stirred for 15 hours. The catalyst was filtered and washed. The filtrate was placed under reduced pressure to distill off the solvent. The residue was purified by silica gel column chromatography (eluent: 19:1 to 8:1 chloroform/methanol). An alcoholic 0.5 N hydrochloric acid (3.9 mL) was added to the fraction containing the title compound in the free form and the mixture obtained was concentrated. The precipitated crystal obtained by filtration was washed with cooled methanol and then dried to give the title compound (370 mg).

$^1$H-NMR (DMSO-$d_6$): 3.00 (3H, s), 3.05–3.53 (4H, m), 4.33–4.42 (2H, m), 5.02 (1H, d, J=9.6), 6.27 (1H, br), 6.75 (1H, dd, J=2.2, 8.5), 6.80 (1H, dd, J=2.2, 8.5), 6.95 (1H, d, J=2.2), 7.13–7.24 (3H, m), 7.31–7.39 (3H, m), 7.88 (1H, d, J=8.5), 8.88 (1H, br), 8.99 (1H, br), 9.24 (1H, br), 9.86 (1H, br), 10.85 (1H, br).

All the publications, patents and patent applications cited herein are incorporated herein by reference in their entirety.

What is claimed is:

1. A process for preparing a compound of the formula (1):

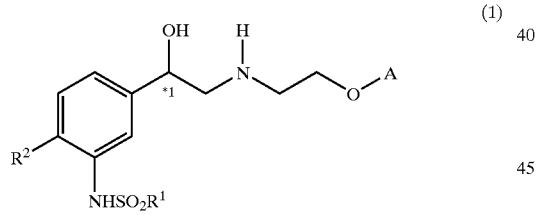
(1)

wherein $R^1$ is lower alkyl or benzyl; $R^2$ is hydrogen, halogen or hydroxyl; *1 is an asymmetric carbon atom; and A is one of the following groups:

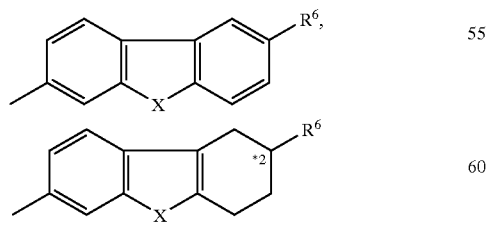

wherein X is NH, O or S; $R^6$ is hydrogen, hydroxyl, amino or acetylamino; and *2 is an asymmetric carbon atom when $R^6$ is not hydrogen, said process comprising:

(a)
i) reacting a compound of the formula (4):

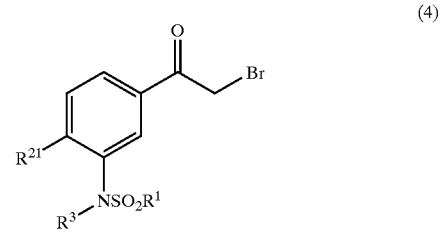
(4)

wherein $R^1$ is as defined above; $R^{21}$ is hydrogen, halogen, hydroxyl or protected hydroxyl; $R^3$ is an amino-protecting group or hydrogen, with a compound of the formula (12):

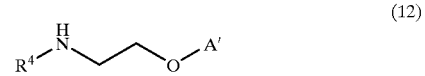
(12)

wherein $R^4$ is an amino-protecting group; and A' is one of the following groups:

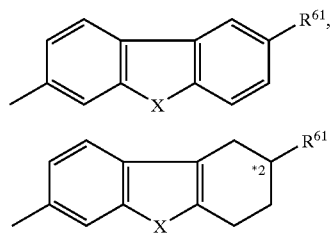

wherein X is NH, O or S; $R^{61}$ is hydrogen, protected hydroxyl, protected amino or an acetylamino group; and *2 is an asymmetric carbon atom when $R^{61}$ is not hydrogen, to give a compound of the formula (3):

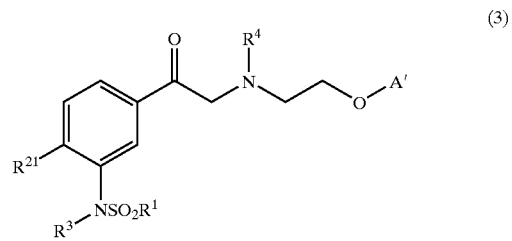
(3)

wherein $R^1$, $R^{21}$, $R^3$, $R^4$ and A' are as defined above; or ii) coupling a compound of the formula (4) with a compound of the formula (14):

(14)

wherein $R^4$ is as defined above, to give a compound of the formula (6):

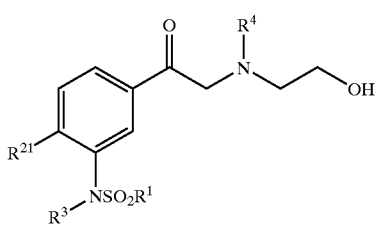

(6)

wherein $R^1$, $R^{21}$, $R^3$ and $R^4$ are as defined above; or iii) further converting the primary hydroxyl group of the compound of the formula (6) into a leaving group $B^3$ to give a compound of the formula (5):

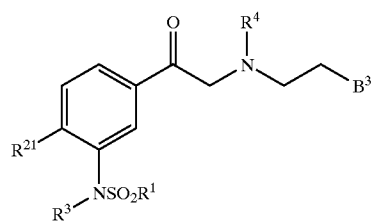

(5)

wherein $R^1$, $R^{21}$, $R^3$ and $R^4$ are as defined above, and $B^3$ is a leaving group; or iv) further reacting the resulting compound of the formula (5) with a compound A'—OH wherein A' is as defined above to give a compound of the formula (3);

(b) reducing the resulting compound of any one of the formulae (3), (5) and (6) to give a compound of the formula (2) as follows:

i) reducing the compound of the formula (3) to give an amino-alcohol of the formula (2):

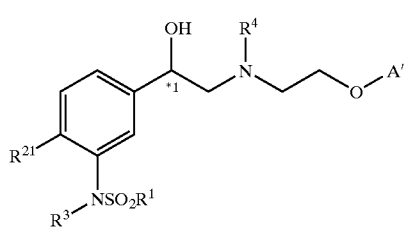

(2)

wherein $R^1$, $R^{21}$, $R^3$, $R^4$ and A' are as defined above, and *1 is an asymmetric carbon atom; or ii) reducing the compound of the formula (5) to give a compound of the formula (7):

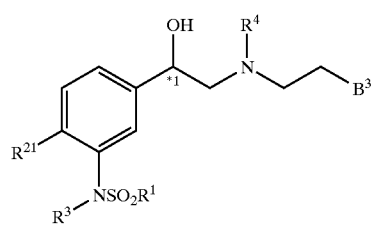

(7)

wherein $R^1$, $R^{21}$, $R^3$, $R^4$ and $B^3$ are as defined above, and *1 is an asymmetric carbon atom, or reducing the compound of the formula (6) to give a compound of the formula (8):

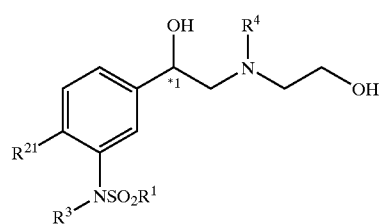

(8)

wherein $R^1$, $R^{21}$, $R^3$ and $R^4$ are as defined above, and *1 is an asymmetric carbon atom, and converting the primary hydroxyl group of the resulting compound of the formula (8) into a leaving group $B^3$ to give a compound of the formula (7), then reacting the compound of the formula (7) obtained by either step as set forth above with a compound A'—OH wherein A' is as defined above to give an amino-alcohol of the formula (2); and (c) simultaneously or sequentially removing the protecting groups of the compound of the formula (2) obtained by any one of processes as set forth above to give a compound of the formula (1).

2. The process as claimed in claim 1, wherein $R^{61}$ is hydrogen.

3. The process as claimed in claim 1, wherein in the step for reducing a compound of the formula (3), (6) or (5) to give an amino-alcohol of the formula (2), (8) or (7), a compound of the formula (3), (6) or (5) is asymmetrically reduced, and the amino-alcohol of the formula (2) and the compound of the formula (1) are one of its optical isomers.

4. A process for preparing a compound of the formula (1):

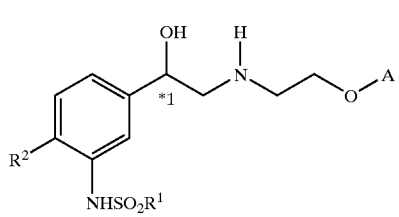

(1)

wherein $R^1$ is lower alkyl or benzyl; $R^2$ is hydrogen, halogen or hydroxyl; *1 is an asymmetric carbon atom; and A is one of the following groups:

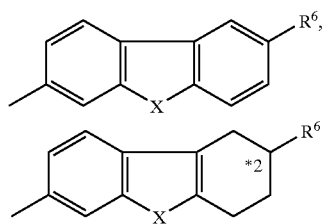

wherein X is NH, O or S; $R^6$ is hydrogen, hydroxyl, amino or acetylamino; and *2 is an asymmetric carbon atom when $R^6$ is not hydrogen, said process comprising:

(a) reacting a compound of the formula (4):

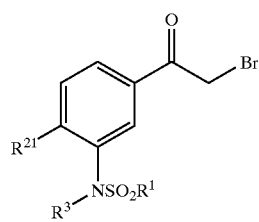

(4)

wherein $R^1$ is as defined above; $R^{21}$ is hydrogen, halogen, hydroxyl or protected hydroxyl; $R^3$ is an amino-protecting group or hydrogen, with a compound of the formula (12):

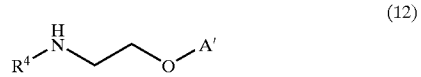

(12)

wherein $R^4$ is an amino-protecting group; and A' is one of the following groups:

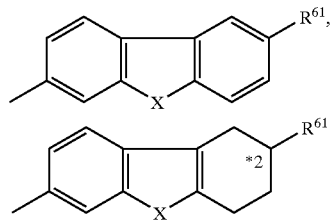

wherein X is NH, O or S; $R^{61}$ is hydrogen, protected hydroxyl, protected amino or an acetylamino group; and *2 is an asymmetric carbon atom when R61 is not hydrogen, to give a compound of the formula (3):

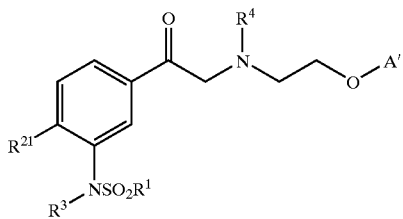

(3)

wherein $R^1$, $R^{21}$, $R^3$, $R^4$ and A' are as defined above;
(b) reducing the resulting compound of the formula (3) to give an amino-alcohol of the formula (2):

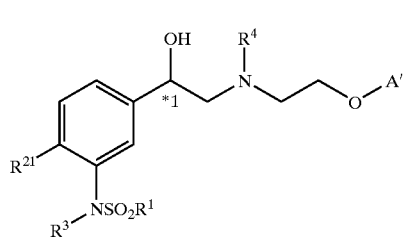

(2)

wherein $R^1$, $R^{21}$, $R^3$, $R^4$ and A' are as defined above, and *1 is an asymmetric carbon atom; and (c) simultaneously or sequentially removing the protecting groups to give a compound of the formula (1).

5. The process as claimed in claim 4, wherein $R^{61}$ is hydrogen.

6. The process as claimed in claim 4, wherein in the step of reducing a compound of the formula (3) to give an amino-alcohol of the formula (2), a compound of the formula (3) is asymmetrically reduced, and the amino-alcohol of the formula (2) and the compound of the formula (1) are one of its optical isomers.

7. The process as claimed in claim 5, wherein in the step of reducing a compound of the formula (3) to give an amino-alcohol of the formula (2), a compound of the formula (3) is asymmetrically reduced, and the amino-alcohol of the formula (2) and the compound of the formula (1) are one of its optical isomers.

8. A process for preparing of a compound of the formula (3):

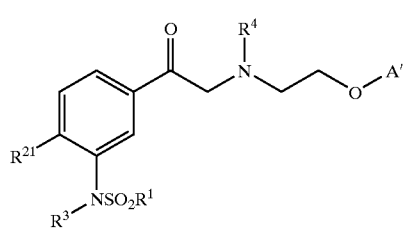

(3)

wherein $R^1$ is lower alkyl or benzyl; $R^{21}$ is hydrogen, halogen, hydroxyl or protected hydroxyl; $R^3$ is an amino-protecting group or hydrogen; $R^4$ is an amino-protecting group; and A' is one of the following groups:

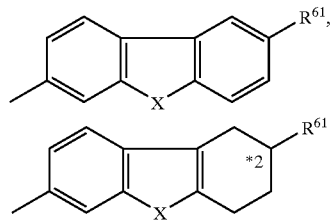

wherein X is NH, O or S; $R^{61}$ is hydrogen, protected hydroxyl, protected amino or an acetylamino group; and *2 is an asymmetric carbon atom when $R^{61}$ is not hydrogen, said process comprising reacting a compound of the formula (4):which comprises reacting a compound of the formula (4):

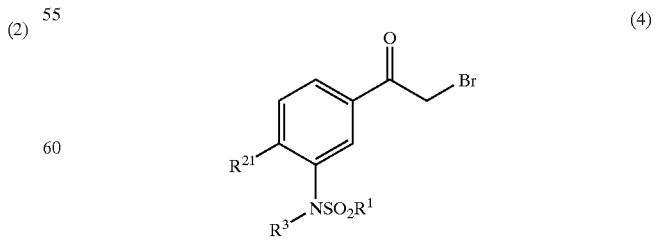

(4)

wherein $R^1$, $R^{21}$ and $R^3$ are as defined above, with a compound of the formula (12):

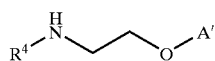

(12)

wherein R⁴ and A' are as defined above, to give a compound of the formula (3).

9. A process for preparing a compound of the formula (2):

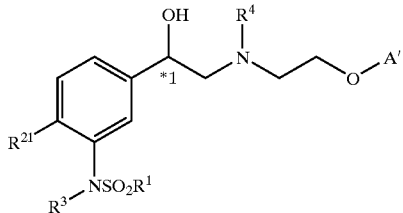

(2)

wherein $R^1$ is lower alkyl or a benzyl; $R^{21}$ is hydrogen, halogen, hydroxyl or protected hydroxyl; $R^3$ is an amino-protecting group or hydrogen; $R^4$ is an amino-protecting group; *1 is an asymmetric carbon atom; and A' is one of the following groups:

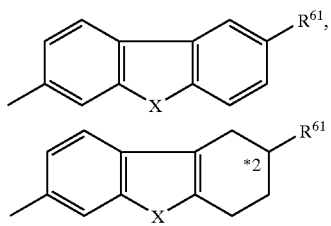

wherein X is NH, O or S; $R^{61}$ is hydrogen, protected hydroxyl, protected amino or an acetylamino group; and *2 is an asymmetric carbon atom when $R^{61}$ is not hydrogen, said process comprising reducing a compound of the formual (3):

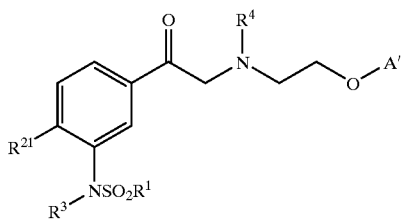

(3)

wherein $R^1$, $R^{21}$, $R^3$, $R^4$ and A' are as defined above, to give a compound of the formula (2).

10. The process as claimed in claim 9, wherein in the step of reducing a compound of the formula (3), a compound of the formula (3) is asymmetrically reduced, and the compound of the formula (2) is one of its optical isomers.

11. A compound of the formula (3) or a salt thereof:

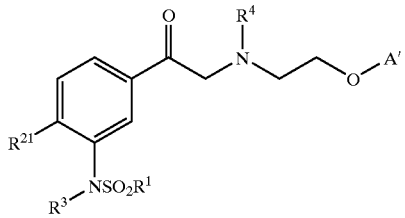

(3)

wherein $R^1$ is lower alkyl or benzyl; $R^{21}$ is hydrogen, halogen, hydroxyl or protected hydroxyl; $R^3$ is an amino-protecting group or hydrogen; $R^4$ is an amino-protecting group; and A' is one of the following groups:

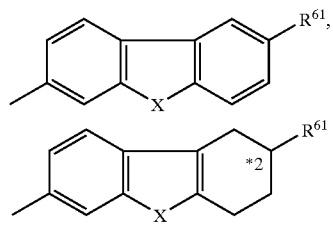

wherein X is NH, O or S; $R^{61}$ is hydrogen, protected hydroxyl, protected amino or an acetylamino group; and *2 is an asymmetric carbon atom when $R^{61}$ is not hydrogen.

12. A compound of the formula (18) or a salt thereof:

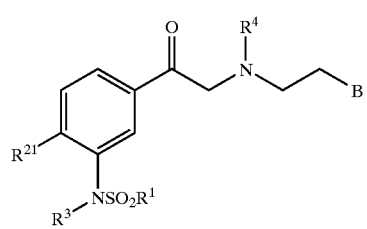

(18)

wherein $R^1$ is lower alkyl or benzyl; $R^{21}$ is hydrogen, halogen, hydroxyl or protected hydroxyl; $R^3$ is an amino-protecting group or hydrogen; $R^4$ is an amino-protecting group; and B is hydroxyl or a leaving group.

13. A compound of the formula (19) or a salt thereof:

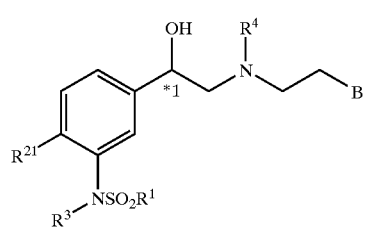

(19)

wherein $R^1$ is lower alkyl or benzyl; $R^{21}$ is hydrogen, halogen, hydroxyl or protected hydroxyl; $R^3$ is hydrogen or an amino-protecting group; $R^4$ is an amino-protecting group; B is hydroxyl or a leaving group; and *1 is an asymmetric carbon atom.

* * * * *